United States Patent
Bondinell et al.

(10) Patent No.: US 6,515,027 B1
(45) Date of Patent: Feb. 4, 2003

(54) SUBSTITUTED BENZANILIDES AS CCR5 RECEPTORS LIGANDS, ANTIINFLAMMATORY AGENTS AND ANTIVIRAL AGENTS

(75) Inventors: William E Bondinell, Wayne, PA (US); James A Chan, West Chester, PA (US)

(73) Assignee: SmithKline Beecham Corp., Philadelphia, PA (US)

( * ) Notice: Subject to any disclaimer, the term of this patent is extended or adjusted under 35 U.S.C. 154(b) by 0 days.

(21) Appl. No.: 09/446,954

(22) PCT Filed: Jul. 1, 1998

(86) PCT No.: PCT/US98/13807

§ 371 (c)(1),
(2), (4) Date: Dec. 29, 1999

(87) PCT Pub. No.: WO99/01127

PCT Pub. Date: Jan. 14, 1999

Related U.S. Application Data

(60) Provisional application No. 60/051,632, filed on Jul. 3, 1997.

(51) Int. Cl.[7] .................. A61K 31/166; A61K 31/4523
(52) U.S. Cl. ....................... 514/617; 514/326; 514/364; 514/651; 564/184; 548/131
(58) Field of Search ................ 514/617, 651, 514/364, 326; 564/184; 548/131

(56) References Cited

U.S. PATENT DOCUMENTS 3,931,195 A     1/1976   Dykstra et al.
4,000,143 A    12/1976   Dykstra et al.
4,091,097 A     5/1978   Umezawa et al.
5,700,818 A    12/1997   Gaster
5,801,170 A  *  9/1998   Gaster et al. ............ 514/236.2

FOREIGN PATENT DOCUMENTS

WO    WO 98 30218    7/1998

* cited by examiner

Primary Examiner—Charanjit S. Aulakh
(74) Attorney, Agent, or Firm—Nora Stein-Fernandez; Stephen A. Venetianer; Charles M. Kinzig

(57) ABSTRACT

This invention relates to substituted benzanilides which are ligands, agonists or antagonists, of the CCR5 receptor. In addition, this invention relates to the treatment and prevention of disease states mediated by CCR5, including, but not limited to, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, and inflammatory bowel disease, all in mammals, by the use of substituted benzanilides which are CCR5 receptor antagonists. Furthermore, since CD8+ T cells have been implicated in COPD, CCR5 may play a role in their recruitment and therefore antagonists to CCR5 could provide potential therapeutic in the treatment of COPD. Also, since CCR5 is a co-receptor for the entry of HIV into cells, selective receptor ligands may be useful in the treatment of HIV infection.

3 Claims, No Drawings

SUBSTITUTED BENZANILIDES AS CCR5 RECEPTORS LIGANDS, ANTIINFLAMMATORY AGENTS AND ANTIVIRAL AGENTS

This application is a 371 of PCT/US98/13807 filed Jul. 1, 1998, now WO 99/01127 published Jan. 14, 1999 and claim benefit of Provisional application No. 60/051,632, filed Jul. 3, 1997.

FIELD OF THE INVENTION

This invention relates to substituted benzanilides which are ligands, agonists or antagonists, of the CC chemokine receptor CC-CKR5 now designated as CCR5 (*Nature Medicine* 1996, 2, 1174–8). In addition, this invention relates to the treatment and prevention of disease states mediated by CCR5.

BACKGROUND OF THE INVENTION

T cells are not only key regulators of the immune response to infectious agents but are believed critical for the initiation and maintenance of the inflammatory reaction in a variety of chronic diseases. Increased numbers or enhanced activation state of T cells, especially CD4+ T cells, have been demonstrated in the synovium of individuals with rheumatoid arthritis (M. J. Elliott and R. N. Maini, *Int. Arch. Allergy Immunol.* 104: 112–1125, 1994), in the bronchial mucosa of asthmatics (C. J. Corrigan and A. B. Kay, *Immunol. Today* 13:501–506, 1992), in the lesions of multiple sclerosis (R. Martin and H. F. McFarland, *Crit. Rev. Clin. Lab. Sci.* 32: 121–182, 1995), in psoriatic lesions (J. L. Jones, J. Berth-Jone, A. Fletcher and P. E. Hutchinson, *J. Pathol.* 174: 77–82, 1994) and in the fatty streaks of atherosclerosis (R. Ross, *Annu. Rev. Physiol.* 57: 791–804, 1995).

T cells, as well as other inflammatory cells, will migrate into tissues in response to the production of a variety chemotactic factors. Among these factors are a superfamily of 8–12 kDa proteins known as the chemokines. These proteins share structural features such as the presence of 3–4 conserved cysteine residues. RANTES, which stands for Regulated upon Activation Normal T cell Expressed and Secreted, is a 8 kDa protein member of CC branch of the chemokine family. These proteins recruit and activate immune and inflammatory cells through an interaction with G-protein coupled receptors. The CC branch is defined by the absence of an intervening amino acid residue between the first two cysteine residues and members of this family predominately elicit the migration of mononuclear cells, eosinophils and basophils (M. Baggiolini, B. Dewald, and B. Moser, *Adv. Immunol.* 55: 97–179, 1994; and J. J. Oppenheim, C. O. C. Zachariae, N. Mukaida, and K. Matsushima, *Annu. Rev. Immunol.* 9: 617–648, 1991).

RANTES potently produces chemotaxis of T cells, basophils, eosinophils, monocytes and mast cells. RANTES was originally identified as gene product induced late after antigen activation of T-cells (T. J. Schall, J. Jongstra, B. J. Dyer, J. Jorgensen, et al., *J. Immunol.* 141:1018–1025, 1988), however, RANTES has been shown to be synthesized and secreted by a diverse group of cells that include epithelial and endothelial cells (C. Stellato, L. A. Beck, G. A. Gorgone, D. Proud, et al., *J. Immunol.* 155: 410–418, 1995; and A. Marfaing-Koka, O. Devergne, G. Gorgone, A. Portier, et al., *J. Immunol.* 154: 1870–1878, 1994), synovial fibroblasts (P. Rathanaswami, M. Hachicha, M. Sadick, T. J. Schall, et al., *J. Biol. Chem.* 268: 5834–5839, 1993) and dermal fibroblasts (M. Sticherling, M. Kupper, F. Koltrowitz, E. Bornscheuer, et al., *J. Invest. Dermatol.* 105: 585–591, 1995), mesangial cells (G. Wolf, S. Aberle, F. Thaiss, et al., *Kidney Int.* 44: 795–804, 1994) and platelets (Y. Koameyoshi, A. Dorschner, A. I. Mallet, E. Christophers, et al., *J. Exp. Med.* 176: 587–592, 1992). In these cells RANTES mRNA is rapidly upregulated in response to IL-1 or TNFa. Although RANTES mRNA is not usually detected in normal tissues (J. M. Pattison, P. J. Nelson, and A. M. Krensky, *Clin. Immunother.* 4: 1–8, 1995), increased mRNA or protein has been found in diseases characterized by a mononuclear infiltrate. For example, RANTES mRNA was visualized using in situ hybridization in renal allografts undergoing rejection (J. M. Pattison, P. J. Nelson, and A. M. Krensky, *Clin. Immunother.* 4: 1–8, 1995; and K. C. Nadeau, H. Azuma and N. I. Tilney, *Proc. Natl. Acad. USA* 92: 8729–8733, 1995) in the skin of atopic dermatitis patients after exposure to antigen (S. Ying, L. Taborda-Barata, Q. Meng, M. Humbert, et al., *J. Exp. Med.* 181: 2153–2159, 1995), and in endothelial cells of coronary arteries undergoing accelerated atherosclerosis after cardiac transplant (J. M. Pattison, P. J. Nelson, and A. M. Krensky, *Clin. Immunother.* 4: 1–8. 1995). Further, increased immunoreactive protein for RANTES has been detected in bronchoalveolar lavage fluid (R. Alam, J. York, M. Boyers, et al.,*Am. J. Resp. Crit. Care Med.* 149: A951, 1994) and sputum from asthmatic individuals (C. M. Gelder, P. S. Thomas, D. H. Yates, I. M. Adcock, et al., *Thorax* 50: 1033–1037, 1995).

Several receptors have been identified that bind RANTES. In particular, CCR5, when expressed in either HEK 293 cells or CHO cells, binds RANTES. This receptor is expressed in T-cells and in monocytes and macrophages, immune/inflammatory cells which are important in the maintenance of a chronic inflammatory reaction. Pharmacological characterization of CCR5 indicates similarities to the RANTES binding site observed on isolated T cells. Therefore, antagonism of RANTES' action on CCR5, as well as antagonism of other natural ligands of CCR5, should inhibit the recruitment of T cells into inflammatory lesions and provide a novel therapeutic approach for the treatment of atopic and autoimmune disorders. Since T cells express CCR5, selective receptor ligands of CCR5, particularly antagonists, are likely to provide beneficial effects in diseases including, but not limited to, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, and inflammatory bowel disease, all in mammals, preferably humans. Furthermore, since CD8+ T cells have been implicated in COPD, CCR5 may play a role in their recruitment and thererfore antagonists to CCR5 could provide potential therpeutic in the treatment of COPD. Also, since CCR5 is a co-receptor for the entry of HIV into cells, selective receptor ligands may be useful in the treatment of HIV infection.

A subset of compounds included in formula (I) have been reported to have 5-HT receptor activity (international application publication number WO 95/15954, published Jun. 15, 1995, international application publication number WO 95/17398, published Jun. 29, 1995, international application publication number WO 95/26328, published Oct. 5, 1995, international application publication number WO 96/06079, published Feb. 29, 1996, GB 2276161 published Sep. 21, 1994, and GB 2276165 published Sep. 21, 1994; international application publication number WO 95/30675 published Nov. 16, 1995; international application publication number WO 95/17401 published Jun. 29, 1995; international application publication number WO 96/31508 published Oct. 10, 1996; international application publication number WO 97/10824 published Mar. 27, 1997; international application publication number WO 96/11934 published Apr. 25, 1996; international application publication number WO 96/19477 published Jun. 27, 1996; international application publication number WO 97/17350 published May 15, 1997; international application publication number WO 97/34900 published Sep. 25, 1997; international application publication number WO 97/34901 published Sep. 25, 1997; international application publication number WO 97/35862 published Oct. 2, 1997; international application publication number WO 97/19070 published May 29, 1997; international application publication number WO 95/32967 published Dec. 7, 1995; international application publication number WO 97/07120 published Feb. 27, 1997; U.S. Pat. No. 3,931,195, issued Jan. 6, 1976; and U.S. Pat. No. 4,000,143, issued Dec. 28, 1976).

Surprisingly, it has now been discovered that this class of non-peptide compounds, in particular substituted benzanilides of formula (I), function as CCR5 receptor ligands, and therefore, have utility in the treatment and prevention of disease states mediated by CCR5 receptor mechanisms.

SUMMARY OF THE INVENTION

The present invention is to the novel use of a CCR5 ligand for the treatment of certain disease states, including, but not limited to, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, inflammatory bowel disease, and HIV infection, all in mammals, preferably humans. The preferred compounds for use as CCR5 ligands are those compounds of Formula (I) as noted herein.

DETAILED DESCRIPTION OF THE INVENTION

It has now been discovered that substituted of formula (I) are CCR5 receptor ligands. It has also now been discovered that selective inhibition of CCR5 receptor mechanisms by treatment with the receptor ligands of formula (I), or a pharmaceutically acceptable salt thereof, represents a novel therapeutic and preventative approach to the treatment of a variety of disease states, including, but not limited to, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, and inflammatory bowel disease, all in mammals, preferably humans. Furthermore, since CD8+ T cells have been implicated in COPD, CCR5 may play a role in their recruitment and thererfore antagonists to CCR5 could provide potential therpeutic in the treatment of COPD. Also, since CCR5 is a co-receptor fro entry into cells, selective receptor ligands may be useful in the treatment of HIV infection.

Compounds for use herein include the CCR5 ligands as described in international application publication number WO 95/15954, published Jun. 15, 1995, (U.S. Ser. No. 08/652,581, filed Jun. 7, 1996); international application publication number WO 95/17398, published Jun. 29, 1995, (U.S. Ser. No. 08/663,291, filed Jun. 21, 1996); international application publication number WO 95/26328, published Oct. 5, 1995, (U.S. Ser. No. 08/718,481, filed Sep. 26, 1996); international application publication number WO 96/06079, published Feb. 29, 1996, (U.S. Ser. No. 08/793,428, filed Feb. 21, 1997); GB 2276161 published Sep. 21, 1994, and GB 2276165 published Sep. 21, 1994; international application publication number WO 95/30675, published Nov. 16, 1995, (U.S. Ser. No. 08/737,147); international application publication number WO 95/17401, published Jun. 29, 1995 (U.S. Ser. No. 08/663,290, filed Jun. 21, 1996); international application publication number WO 96/31508, published Oct. 10, 1996 (U.S. Ser. No. 08/930,848, filed Oct. 7, 1997); international application publication number WO 97/10824, published Mar. 27, 1997 (U.S. Ser. No. 09/043,346); international application publication number WO 96/11934, published Apr. 25, 1996, (U.S. Ser. No. 08/817,619); international application publication number WO 96/19477, published Jun. 27, 1996 (U.S. Ser. No. 08/849,932); international application publication number WO 97/17350, published May 15, 1997 (U.S. Ser. No. 09/068,382, filed May 8, 1998); international application publication number WO 97/34900, published Sep. 25, 1997; international application publication number WO 97/34901, published Sep. 25, 1997; international application publication number WO 97/35862, published Oct. 2, 1997; international application publication number WO 97/19070, published May 29, 1997 (U.S. Ser. No. 09/077,263); international application publication number WO 95/32967, published Dec. 7, 1995 (U.S. Ser. No. 08/737,660); international application publication number WO 97/07120, published Feb. 27, 1997 (U.S. Ser. No. 09/011,338, filed Feb. 11, 1998); U.S. Pat. No. 3,931,195, issued Jan. 6, 1976; and U.S. Pat. No. 4,000,143, issued Dec. 28, 1976.

Preferred compounds for use as CCR5 ligands are those compounds of Formula (I) as noted herein.

Each of these references is incorporated herein in their entirety.

A preferred group of compounds for use herein are those compounds of the formula (I) or a pharmaceutically acceptable salt thereof:

Ar—A—E               Formula I in which Ar represents a group selected from (i), (ii) or (iii);

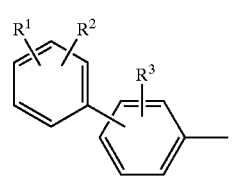

(i)

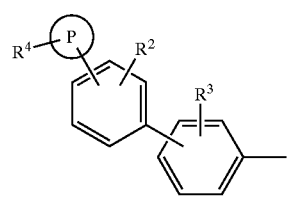

(ii)

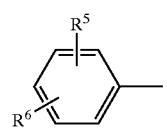

(iii)

in which:

$R^1$ and $R^2$ are independently hydrogen, $C_{1-6}$alkyl, $C_{2-6}$alkenyl, $C_{2-6}$alkynyl, $C_{3-7}$cycloalkyl, $C_{3-6}$cycloalkenyl, aryl, $(CH_2)_aNR^7R^8$, $(CH_2)_aNR^7COR^9$, $(CH_2)_aNR^7CO_2R^{10}$, $(CH_2)_aNR^7SO_2R^{11}$, $(CH_2)_aCONR^{12}R^{13}$, hydroxy $C_{1-6}$alkyl, $C_{1-4}$alkoxyalkyl (optionally substituted by a $C_{1-4}$alkoxy or hydroxy group), $(CH_2)_bCO_2C_{1-6}$alkyl, $(CH_2)_bOC(O)R^{14}$, $CR^{15}=NOR^{16}$, $CNR^{15}=NOR^{16}$, $COR^{17}$, $CONR^{12}R^{13}$, $CONR^{12}(CH_2)_cOC_{1-4}$alkyl, $CONR^{12}(CH_2)_aCO_2R^{18}$, $CONHNR^{19}R^{20}$, $CONR^{12}SO_2R^{21}$, $CO_2R^{22}$, cyano, trifluoromethyl, $NR^7R^8$, $NR^7COR^9$, $NR^{23}CO(CH_2)_aNR^{23}R^{24}$, $NR^{23}CONR^{23}R^{24}$, $NR^7CO_2R^{10}$, $NR^7SO_2R^{11}$, $N=CNR^{23}NR^{23}R^{24}$, nitro, hydroxy, $C_{1-6}$alkoxy, hydroxy$C_{1-6}$alkoxy, $C_{1-6}$alkoxy$C_{1-6}$alkoxy, $OC(O)NR^{25}R^{26}$, $SR^{27}$, $SOR^{28}$, $SO_2R^{28}$, $SO_2NR^{25}R^{26}$ or halogen;

a is 1, 2, 3 or 4;

$R^7$ and $R^8$ are independently hydrogen or $C_{1-6}$alkyl, or $NR^7R^8$ forms a heterocyclic ring which has 5 or 6 ring members which, may optionally be substituted by an oxo group and, when there are 6 ring members, may optionally contain in the ring one oxygen or sulfur atom;

$R^9$ is hydrogen, $C_{1-6}$alkyl or $C_{1-4}$alkoxyalkyl;

$R^{10}$ is $C_{1-6}$alkyl;

$R^{11}$ is $C_{1-6}$alkyl or phenyl;

$R^{12}$ and $R^{13}$ are independently hydrogen or $C_{1-6}$alkyl, or $NR^{12}R^{13}$ forms a saturated heterocyclic ring which has 5 or 6 members which, when there are 6 ring members, may optionally contain in the ring one oxygen or sulfur atom;

b is 0, 1, 2 or 3;

$R^{14}$ is $C_{1-4}$alkyl, optionally substituted by a $C_{1-6}$alkoxy;

$R^{15}$ and $R^{16}$ are independently hydrogen or $C_{1-6}$alkyl;

$R^{17}$ is hydrogen or $C_{1-6}$alkyl;

c is 1, 2 or 3;

$R^{18}$ is hydrogen or $C_{1-6}$alkyl;

$R^{19}$ and $R^{20}$ are independently hydrogen or $C_{1-6}$alkyl;

$R^{21}$ is hydrogen or $C_{1-6}$alkyl;

$R^{22}$ is hydrogen or $C_{1-6}$alkyl optionally substituted with one or two substituents selected from $C_{1-6}$alkyl, $C_{1-6}$alkoxy, hydroxy, or $NR^7R^8$;

$R^{23}$ and $R^{24}$ are independently hydrogen or $C_{1-6}$alkyl;

$R^{25}$ and $R^{26}$ are independently hydrogen or $C_{1-6}$alkyl, or $NR^{25}R^{26}$ forms a saturated heterocyclic ring which has 5 or 6 members which, when there are 6 ring members, may optionally contain in the ring one oxygen or sulfur atom;

$R^{27}$ is hydrogen or $C_{1-6}$alkyl;

$R^{28}$ is $C_{1-6}$alkyl;

P is a 5 to 7-membered heterocyclic ring containing 1 to 4 heteroatoms selected from oxygen, nitrogen or sulfur;

$R^3$ and $R^4$ are independently hydrogen, $C_{1-6}$alkyl, $C_{3-7}$cycloalkyl, $C_{3-6}$cycloalkenyl, hydroxy$C_{1-6}$alkyl, $C_{1-6}$alkylO$C_{1-6}$alkyl, $CONR^{29}R^{30}$, $CO_2R^{31}$, cyano, aryl, trifluoromethyl, $NR^{29}R^{30}$, nitro, hydroxy, $C_{1-6}$alkoxy, acyloxy or halogen;

$R^{29}$, $R^{30}$ and $R^{31}$ are independently hydrogen or $C_{1-6}$alkyl;

$R^5$ is hydrogen, $C_{1-6}$alkyl, $C_{1-6}$alkoxy or halogen;

$R^6$ is hydrogen, $C_{1-6}$alkyl, $C_{3-7}$cycloalkyl (optionally substituted by a hydroxy or an oxo group), hydroxy$C_{1-6}$alkyl, hydroxy$C_{3-6}$alkenyl, hydroxy$C_{3-6}$alkynyl, $(CH_2)_dOR^{32}$, $(CH_2)_dCOR^{33}$, $(CH_2)_dCR^{34}=NOR^{35}$, $CONR^{36}R^{37}$, $CO_2R^{38}$, hydroxy, $O(CH_2)_eR^{39}$, $NR^{36}R^{37}$, $SR^{40}$, $SO_2NR^{41}R^{42}$ or halogen;

d is 0, 1, 2, 3, 4, 5, or 6;

$R^{32}$ is $C_{1-6}$alkyl, hydroxy$C_{1-6}$alkyl, or $C_{1-4}$alkanoyl;

$R^{33}$ is hydrogen or $C_{1-6}$alkyl;

$R^{34}$ is hydrogen or $C_{1-6}$alkyl;

$R^{35}$ is hydrogen or $C_{1-6}$alkyl;

$R^{36}$ and $R^{37}$ are independently hydrogen or $C_{1-6}$alkyl or $NR^{36}R^{37}$ forms a saturated heterocyclic ring which has 5 or 6 members, may optionally be substituted by an oxo group and, when there are 6 ring members, may optionally contain one oxygen or sulfur atom or an NH or $NR^{43}$ where $R^{43}$ is $C_{1-6}$alkyl, $COR^{44}$ or $CO_2R^{45}$ where $R^{44}$ and $R^{45}$ are independently hydrogen or $C_{1-6}$alkyl;

$R^{38}$ is hydrogen or $C_{1-6}$alkyl;

e is 1, 2, 3, 4, 5 or 6;

$R^{39}$ is $C_{1-6}$alkoxy, $CO_2H$, $CO_2C_{1-6}$alkyl or $CONR^{36}R^{37}$;

$R^{40}$ is $C_{1-6}$alkyl;

$R^{41}$ and $R^{42}$ are independently hydrogen or $C_{1-6}$alkyl;

alternatively, $R^5$ and $R^6$ form a fused benzo ring optionally substituted with $C_{1-6}$ alkyl, $C_{1-6}$alkoxy or halogen;

when Ar is (i), (ii) or (iii), and A is $CONR^{46}$, NHCO, —NHCH$_2$, or CH$_2$NH, where $R^{46}$ is hydrogen or $C_{1-6}$alkyl, E represents (a):

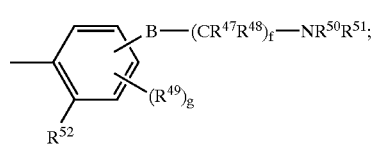

(a)

in which $R^{47}$ and $R^{48}$ are independently hydrogen or $C_{1-6}$alkyl;

$R^{49}$ is hydrogen, $C_{1-6}$alkyl, $CO_2R^{53}$, $NHCO_2R^{54}$, hydroxy, $C_{1-6}$alkoxy or halogen where $R^{53}$ is hydrogen or $C_{1-6}$alkyl and $R^{54}$ is $C_{1-6}$alkyl;

$R^{50}$ and $R^{51}$ are independently hydrogen, $C_{1-6}$alkyl, $C_{3-7}$cycloalkyl, aralkyl, or together with the nitrogen atom to which they are attached form an optionally substituted 5- to 7-membered heterocyclic ring containing one to two heteroatoms selected from oxygen, nitrogen or sulfur;

B is oxygen, $S(O)_h$ where h is 0, 1 or 2, $CR^{55}=CR^{56}$ or $CR^{55}R^{56}$ where $R^{55}$ and $R^{56}$ are independently hydrogen or $C_{1-6}$alkyl, or B is $NR^{57}$ where $R^{57}$ is hydrogen, $C_{1-6}$alkyl or phenyl$C_{1-6}$alkyl;

$R^{52}$ is hydrogen or $R^{52}$ taken together with $R^{46}$ forms a group D where D is $(CR^{58}R^{59})_i$ where i is 2, 3 or 4 and $R^{58}$ and $R^{59}$ are independently hydrogen or $C_{1-6}$alkyl or D is $(CR^{58}R^{59})_j$—G where j is 0, 1, 2 or 3 and G is oxygen, sulfur or $CR^{58}=CR^{59}$;

f is 1 to 4; and g is 1 or 2;

when Ar is (i), (ii) or (iii), and A is $CONR^{60}$, NHCO, or CH$_2$NH, where $R^{60}$ is hydrogen or $C_{1-6}$alkyl, E represents (b):

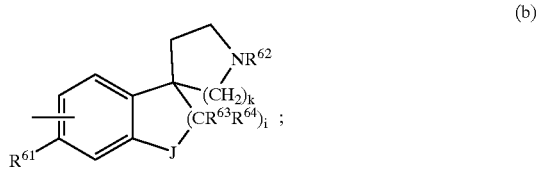

(b)

$R^{61}$ is hydrogen or $C_{1-6}$alkyl or $R^{61}$ and $R^{60}$ together form a group —K— where K is $(CR^{65}R^{66})_m$ where m is 2, 3, or 4 and $R^{65}$ and $R^{66}$ are independently hydrogen or $C_{1-6}$alkyl or K is $(CR^{65}R^{66})_n$—L where n is 0, 1, 2, or 3 and L is oxygen, sulfur or $CR^{65}=CR^{66}$;

$R^{62}$ is hydrogen or $C_{1-6}$alkyl;

$R^{63}$ and $R^{64}$ are independently hydrogen or $C_{1-6}$alkyl;

J is oxygen, $CR^{67}R^{68}$ or $NR^{69}$ where $R^{67}$, $R^{68}$ and $R^{69}$ are independently hydrogen of $C_{1-6}$alkyl or J is a group $S(O)_m$ where m is 0, 1 or 2;

k is 1, 2 or 3;

l is 1, 2 or 3;

when Ar is (i), (ii) or (iii), and A is $CONR^{70}$, NHCO, —$NHCH_2$, or $CH_2NH$, where $R^{70}$ is hydrogen or $C_{1-6}$alkyl, E represents (c):

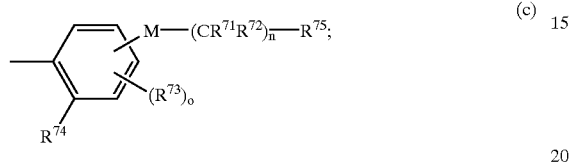

in which:

M is oxygen, $S(O)_p$ where p is 0, 1 or 2, $CR^{76}=CR^{77}$ or $CR^{76}R^{77}$ where $R^{76}$ and $R^{77}$ are independently hydrogen or $C_{1-6}$alkyl, or M is $NR^{78}$ where $R^{78}$ is hydrogen or alkyl;

$R^{71}$ and $R^{72}$ are independently hydrogen or $C_{1-6}$alkyl;

$R^{73}$ is hydrogen, $C_{1-6}$alkyl, $CO_2R^{79}$, $NHCO_2R^{80}$, hydroxy, $C_{1-6}$alkoxy or halogen where $R^{79}$ is hydrogen or $C_{1-6}$alkyl and $R^{80}$ is $C_{1-6}$alkyl;

$R^{74}$ is hydrogen or together with $R^{70}$ forms a group Q where Q is $CR^{81}=CR^{82}$, $CR^{81}=CR^{82}CR^{81}R^{82}$ or $(CR^{81}R^{82})_q$ where q is 2 or 3 and $R^{81}$ and $R^{82}$ are independently hydrogen or $C_{1-6}$alkyl;

n is 0, 1, 2 or 3;

o is 1 or 2;

$R^{75}$ is a group of formula (d):

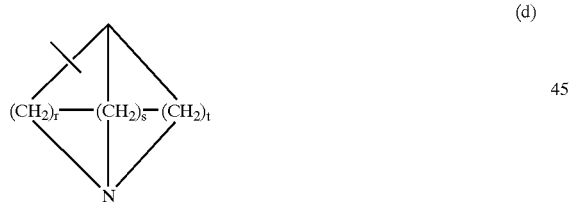

where r, s and t are independently integers having the value 1, 2 or 3;

or $R^{75}$ is a group of formula (e):

where u is 0, 1, 2 or 3 and $R^{83}$ is hydrogen or $C_{1-6}$alkyl;

when Ar is (i), (ii), or (iii), and A is CONH, NHCO or $CH_2NH$, E represents (f):

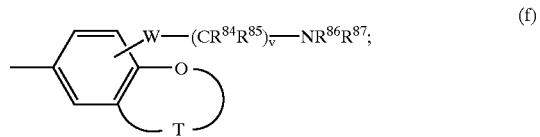

$R^{84}$ and $R^{85}$ are independently hydrogen or $C_{1-6}$alkyl;

$R^{86}$ and $R^{87}$ are independently hydrogen, $C_{1-6}$alkyl, $C_{3-7}$cycloalkyl, aralkyl, or together with the nitrogen atom to which they are attached form an optionally substituted 5- to 7-membered heterocyclic ring containing one to two heteroatoms selected from oxygen, nitrogen or sulfur;

T is —$(CR^{88}R^{89})_w$— or —$O(CR^{88}R^{89})_x$— where $R^{88}$ and $R^{89}$ are independently hydrogen or $C_{1-6}$alkyl where w is 2 or 3 and x is 1, 2 or 3;

v is 1 to 4; and

W is oxygen, $S(O)_y$ where y is 0, 1 or 2, or W is $NR^{90}$ where $R^{90}$ is hydrogen or $C_{1-6}$alkyl, or W is $CR^{91}=CR^{92}$ or $CR^{91}R^{92}$ where $R^{91}$ and $R^{92}$ are independently hydrogen or $C_{1-6}$alkyl;

when Ar is (i), (ii) or (iii), and A is $CONR^{93}$, NHCO, or $CH_2NH$ where $R^{93}$ is hydrogen or $C_{1-6}$alkyl, E represents a group (g):

$R^{94}$ is hydrogen, halogen, hydroxy, $C_{1-6}$alkyl or $C_{1-6}$alkoxy or $R^{94}$ and $R^{93}$ taken together from a group —X— where X is $(CR^{97}R^{98})_{aa}$ where aa is 2, 3 or 4 and $R^{97}$ and $R^{98}$ are independently hydrogen or $C_{1-6}$alkyl or X is $(CR^{97}R^{98})_{ab}$— Y were ab is 0, 1, 2 or 3 and Y is oxygen, sulfur or $CR^{97}=CR^{98}$;

$R^{95}$ is hydrogen, $C_{1-6}$alkyl, $CO_2R^{99}$, $NHCO_2R^{100}$, hydroxy, $C_{1-6}$alkoxy or halogen where $R^{95}$ is hydrogen or $C_{1-6}$alkyl and $R^{100}$ is $C_{1-6}$alkyl;

z is 1 or 2; and $R^{96}$ is an optionally substituted 5 to 7-membered saturated or partially saturated heterocyclic ring containing 1 to 3 heteroatoms selected from nitrogen, oxygen or sulfur or $R^{96}$ is an optionally substituted 6,6 or 6,5 bicyclic ring containing a nitrogen atom and optionally a further heteroatom selected from oxygen, nitrogen or sulfur;

when Ar is (i), (ii) or (iii) and A is $CONR^{101}$, NHCO, or $CH_2NH$, where $R^{101}$ is hydrogen or $C_{1-6}$alkyl, E represents group (h):

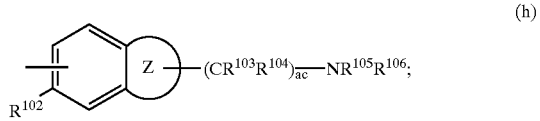

$R^{102}$ is hydrogen or $C_{1-6}$alkyl, $C_{1-6}$alkoxy or halogen, or $R^{102}$ together with $R^{101}$ form a group —AA— where AA is $(CR^{107}R^{108})$ad where ad is 1, 2 or 3 and $R^{107}$ and $R^{108}$ are independently hydrogen or $C_{1-6}$alkyl or AA is $(CR^{107}=CR^{108})_{ae}$—AB where ae is 0, 1 or 2 and AB is oxygen, sulfur, $CR^{107}=CR^{108}$, $CR^{107}=N$, $CR^{102}NR^{108}$ or N=N;

$R^{103}$ and $R^{104}$ are independently hydrogen or $C_{1-6}$alkyl;

R$^{105}$ and R$^{106}$ are independently hydrogen, C$_{1-6}$alkyl, C$_{3-7}$cycloalkyl, aralkyl, or together with the nitrogen atom to which they are attached form an optionally substituted 5- to 7-membered heterocyclic ring containing one to two heteroatoms selected from oxygen, nitrogen or sulfur;

ac is 0 to 4;

Z is an optionally substituted 5 to 7-membered heterocyclic ring containing 1 to 3 heteroatoms selected from oxygen, nitrogen or sulfur;

when Ar is (i), (ii) or (iii) and A is CONR$^{109}$, NHCO, or CH$_2$NH where R$^{109}$ is hydrogen or C$_{1-6}$alkyl, E represents group (i):

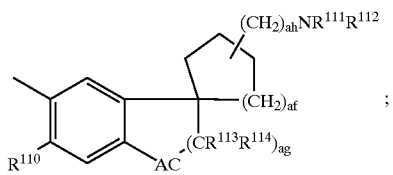

(i)

R$^{110}$ is hydrogen or C$_{1-6}$alkyl or R$^{110}$ and R$^{109}$ together form a group —AD— where AD is (CR$^{115}$R$^{116}$)$_{ah}$ where ah is 2, 3 or 4 and R$^{115}$ and R$^{116}$ are independently hydrogen or C$_{1-6}$alkyl or AD is (CR$^{115}$R$^{116}$)$_{ai}$—AE were ai is 0, 1, 2 or 3 and AE is oxygen, sulfur or CR$^{115}$=CR$^{116}$;

R$^{111}$ and R$^{112}$ are independently hydrogen, C$_{1-6}$alkyl, C$_{3-7}$cycloalkyl, aralkyl, or together with the nitrogen atom to which they are attached form an optionally substituted 5- to 7-membered heterocyclic ring containing one to two heteroatoms selected from oxygen, nitrogen or sulfur;

R$^{113}$ and R$^{114}$ are independently hydrogen or C1–6alkyl;

AC is oxygen, CR$^{117}$R$^{118}$ or NR$^{119}$ where R$^{117}$, R$^{118}$ and R$^{119}$ are independently hydrogen or C1–6alkyl or AC is a group S(O)$_{aj}$ where aj is 0, 1 or 2;

af is 1, 2 or 3;

ag is 1, 2, 3, or 4; and ah is 0, 1, 2, 3 or 4.

Suitably, when Ar is (i) or (ii), the terminal phenyl group in (i) and (ii) can be attached to the phenyl group bearing group A in any position. Preferably the terminal phenyl ring is attached to the phenyl bearing group A in a position meta or para to group A, more preferably para to group A.

Suitably P is a 5- to 7-membered heterocyclic ring containing 1 to 4 heteroatoms selected from oxygen, nitrogen or sulfur. Examples of suitable heterocyclic rings include thienyl, furyl, triazolyl, diazolyl, imidazolyl, oxadiazolyl, isothiazolyl, isoxazolyl, thiadiazolyl, pyridyl, pyrimidyl, pyrazinyl and dioxanyl. Suitably the heterocyclic rings can be linked to the remainder of the molecule via a carbon atom or, when present, a nitrogen atom. Preferably P is oxadiazolyl.

Suitably, when Ar is (iii), R$^6$ can be attached to the phenyl ring in any position. Preferably, R$^6$ is attached meta or para to group A. More preferably, R$^6$ is attached at the para to group A.

Suitably R$^1$ and R$^2$ are independently hydrogen, C$_{1-6}$alkyl, C$_{2-6}$alkenyl, C$_{2-6}$alkynyl, C$_{3-7}$cycloalkyl, C$_{3-6}$cycloalkenyl, aryl, (CH$_2$)$_a$NR$^7$R$^8$, (CH$_2$)$_a$NR$^7$COR$^9$, (CH$_2$)$_a$NR$^7$CO$_2$R$^{10}$, (CH$_2$)$_a$NR$^7$SO$_2$R$^{11}$, (CH$_2$)$_a$CONR$^{12}$R$^{13}$, hydroxyC$_{1-6}$alkyl, C$_{1-4}$alkoxyalkyl (optionally substituted by a C$_{1-4}$alkoxy or hydroxy group), (CH$_2$)$_a$CO$_2$C$_{1-6}$alkyl, (CH$_2$)$_b$OC(O)R$^{14}$, CR$^{15}$=NOR$^{16}$, CNR$^{15}$=NOR$^{16}$, COR$^{17}$, CONR$^{12}$R$^{13}$, CONR$^{12}$(CH$_2$)$_c$OC$_{1-4}$alkyl, CONR$^{12}$(CH$_2$)$_a$CO$_2$R$^{18}$, CONHNR$^{19}$R$^{20}$, CONR$^{12}$SO$_2$R$^{21}$, CO$_2$R$^{22}$, cyano, trifluoromethyl, NR$^7$R$^8$, NR$^7$COR$^9$, NR$^{23}$CO(CH$_2$)$_a$NR$^{23}$R$^{24}$, NR$^{23}$CONR$^{23}$R$^{24}$, NR$^7$CO$_2$R$^{10}$, NR$^7$SO$_2$R$^{11}$, N=CNR$^{23}$NR$^{23}$R$^{24}$, nitro, hydroxy, C$_{1-6}$alkoxy, hydroxyC$_{1-6}$alkoxy, C$_{1-6}$alkoxyC$_{1-6}$alkoxy, OC(O)NR$^{25}$R$^{26}$, SR$^{27}$, SOR$^{28}$, SO$_2$R$^{28}$, SO$_2$NR$^{25}$R$^{26}$ or halogen. Preferably at least one of R$^1$ or R$^2$ are independently, hydrogen, C$_{1-6}$alkyl, preferably methyl, C$_{1-6}$alkoxy, preferably methoxy, preferably in the 3-position, hydroxy, preferably in the 3-position, cyano, preferably in the 4-position, and (CH$_2$)$_b$OC(O)R$^{14}$, wherein b is preferably 0, and R$^{14}$ is preferably ethyl.

Suitably R$^3$ and R$^4$ are independently hydrogen, C$_{1-6}$alkyl, C$_{3-7}$cycloalkyl, C$_{3-6}$cycloalkenyl, hydroxyC$_{1-6}$alkyl, C$_{1-6}$alkylOC$_{1-6}$alkyl, CONR$^{29}$R$^{30}$, CO$_2$R$^{31}$, cyano, aryl, trifluoromethyl, NR$^{29}$R$^{30}$, nitro, hydroxy, C$_{1-6}$alkoxy, acyloxy or halogen. Preferably R$^3$ is hydrogen and C$_{1-6}$alkyl, more preferably methyl. R$^4$—P is preferably CH$_3$-oxadiazolyl.

Suitably R$^6$ is hydrogen, C$_{1-6}$alkyl, C$_{3-7}$cycloalkyl (optionally substituted by a hydroxy or an oxo group), hydroxyC$_{1-6}$alkyl, hydroxyC$_{3-6}$alkenyl, hydroxyC$_{3-6}$alkynyl, (CH$_2$)$_d$OR$^{32}$, (CH$_2$)$_d$COR$^{33}$, (CH$_2$)$_d$CR$^{34}$=NOR$^{35}$, CONR$^{36}$R$^{37}$, CO$_2$R$^{38}$, hydroxy, O(CH$_2$)$_e$R$^{39}$, NR$^{36}$R$^{37}$, SR$^{40}$, SO$_2$NR$^{41}$R$^{42}$ or halogen. Preferably, R$^6$ is C$_{3-7}$cycloalkyl, more preferably cyclohexyl, or halogen, more preferably iodo.

Preferably R$^7$ and R$^8$ are independently hydrogen or C$_{1-6}$alkyl;

Preferably R$^9$ is hydrogen or C$_{1-6}$alkyl;

Preferably R$^{11}$ is C$_{1-6}$alkyl;

Preferably R$^{12}$ and R$^{13}$ are independently hydrogen or C$_{1-6}$alkyl;

Preferably R$^{14}$ is C$_{1-6}$alkyl;

Preferably R$^{22}$ is hydrogen or C$_{1-6}$alkyl;

Preferably R$^{25}$ and R$^{26}$ are independently hydrogen or C$_{1-6}$alkyl.

Suitably E represents (a). When E represents (a), the groups —B(CR$^{47}$R$^{48}$)$_f$—NR$^{50}$R$^{51}$ and R$^{49}$ can be attached to the phenyl ring at any position. Preferably the group —B(CR$^{47}$R$^{48}$)$_f$—NR$^{50}$R$^{51}$ is located meta or para to the amide linkage, more preferably meta. Preferably the group R$^{49}$ is located para to the amide linkage. Preferably the group R$^{49}$ is alkoxy, more preferably methoxy, or halogen, more preferably iodo. Preferably, B is oxygen or CR$^{55}$R$^{56}$. Preferably, f is 2 or 3. Suitably, R$^{50}$ and R$^{51}$ are C$_{1-6}$alkyl, preferably isopropyl, or tert-butyl; C$_{3-7}$cycloalkyl, preferably cyclohexyl; or together with the nitrogen atom to which they are attached, form a 5- to 7-membered heterocyclic ring.

Preferred compounds of formula (I) are wherein, E represents (a), and wherein B is oxygen, CR$^{55}$R$^{56}$ is CH$_2$ and f is 2, and wherein B is CH$_2$, CR$^{55}$R$^{56}$ is CH$_2$ and f is 2, and wherein B is oxygen, CR$^{55}$R$^{56}$ is CH$_2$ and f is 3. Particularly preferred is a compound of formula (I) wherein B is oxygen, CR$^{55}$R$^{56}$ is CH$_2$ and f is 2. R$^{52}$ is preferably hydrogen.

Other preferred compounds of formula (I) are wherein, E represents (a) and preferably R$^{50}$ and R$^{51}$ are isopropyl, R$^{50}$ is isopropyl and R$^{51}$ is tert-butyl or cyclohexyl, or NR$^{50}$R$^{51}$ is 2,2,6,6-tetramethylpiperidine. More preferably, R$^{50}$ and R$^{51}$ are isopropyl, R$^{50}$ is isopropyl and R$^{51}$ is tert-butyl, or NR$^{50}$R$^{51}$ is 2,2,6,6-tetramethylpiperidine. Preferably R$^{49}$ is methoxy.

When E represents (b), k is preferably 1, J is preferably oxygen, and R$^{62}$ is preferably C$_{1-6}$alkyl, more preferably methyl or isopropyl.

When E represents (c), n is preferably 1, M is preferably oxygen, $R^{71}$ and $R^{72}$ are preferably hydrogen, $R^{73}$ is preferably para-alkoxy, more preferably para-$OCH_3$, $R^{74}$ is preferably hydrogen, and $R^{75}$ is preferably a group of formula (e) wherein u is 2, and $R^{83}$ is preferably $C_{1-6}$alkyl, more preferably methyl.

The term "$C_{1-6}$alkyl" is used herein at all occurrences to mean a straight or branched chain radical of 1 to 6 carbon atoms, unless the chain length is limited thereto, including, but not limited to methyl, ethyl, n-propyl, isopropyl, n-butyl, sec-butyl, isobutyl, tert-butyl, and the like.

The terms "halo" or "halogen" are used interchangeably herein at all occurrences to mean radicals derived from the elements chlorine, fluorine, iodine and bromine.

The terms "cycloalkyl" and "cyclic alkyl" are used herein at all occurrences to mean cyclic radicals, preferably comprising 3 to 7 carbon atoms which may be mono- or bicyclo-fused ring systems which may additionally include unsaturation, including, but not limited to, cyclopropyl, cyclopentyl, cyclohexyl, 1,2,3,4-tetrahydronaphthyl, and the like.

The term "alkenyl" is used herein at all occurrences to mean a straight or branched chain radical of 2 to 6 carbon atoms, unless the length is limited thereto, wherein there is at least one double bond between two of the carbon atoms in the chain, including, but not limited to, ethenyl, 1-propenyl, 2-propenyl, 2-methyl-1-propenyl, 1-butenyl, 2-butenyl, and the like.

The term "cycloalkenyl" is used herein to mean cyclic radicals, preferably of 5 to 8 carbons, which have at least one double bond between two of the carbon atoms in the ring, including but not limited to cyclopentenyl, cyclohexenyl, and the like.

The term "alkynyl" is used herein at all occurrences to mean a straight or branched chain radical of 2 to 8 carbon atoms, unless the chain length is limited thereto, wherein there is at least one triple bond between two of the carbon atoms in the chain, including, but not limited to, acetylene, 1-propylene, 2-propylene, and the like.

The term "aryl" is used herein at all occurrences to mean 5–14-membered substituted or unsubstituted aromatic ring(s) or ring systems which may include bi- or tri-cyclic systems, including, but not limited to phenyl, naphthyl, and the like.

The term "aralkyl" is used herein at all occurrences to mean an aryl moiety as defined above, which is connected to an alkyl moiety as defined above, for example, benzyl or phenethyl, and the like.

The term "alkoxy" is used herein at all occurrences to mean a straight or branched chain radical of 1 to 6 carbon atoms, unless the chain length is limited thereto, bonded to an oxygen atom, including, but not limited to, methoxy, ethoxy, n-propoxy, isopropoxy, and the like.

The terms "hydroxy$C_{1-6}$alkyl" and "hydroxyalkyl" are used herein interchangeably to mean an hydroxyl group bonded to a $C_{1-6}$alkyl group as defined above, including, but not limited to methanol, ethanol, n-propanol, isopropanol, n-butanol, sec-butanol, isobutanol, tert-butanol, and the like.

The term "$C_{1-4}$alkoxyalkyl" is used herein at all occurrences to mean a $C_{1-4}$alkoxy group as defined above bonded to an alkyl group as defined above, such as an ether, e.g., $CH_3$—$CH_2$—O—$CH_2$—$CH_2$—$CH_3$.

The term "hydroxy$C_{1-6}$alkoxy" is used herein at all occurrences to mean an hydroxyl group bonded to an alkoxy group as defined above, e.g., HO—$CH_2$—CH(OH)$CH_3$.

The term "$C_{1-6}$alkoxy$C_{1-6}$alkoxy" is used herein at all occurences to mean an alkoxy group as defined above, substituted with an alkoxy group as defined above.

The term "acyloxy" is used herein at all occurrences to mean a moiety —O—C(O)—R, wherein R is hydrogen or $C_{1-6}$alkyl.

The term "$C_{1-4}$alkanoyl" is used herein at all occurrences to mean a C(O)$C_{1-4}$alkyl group wherein the alkyl portion is as defined above.

The term "heteroatom" is used herein at all occurrences to mean an oxygen atom, a sulfur atom or a nitrogen atom. It will be recognized that when the heteroatom is nitrogen, it may form an $NR_aR_b$ moiety, wherein $R_a$ and $R_b$ are, independently, hydrogen or $C_1$ to $C_6$ alkyl, or together with the nitrogen to which they are bound, form a saturated or unsaturated 5-, 6- or 7-membered ring, including, but not limited to, pyrrolidine, piperidine, piperazine, morpholine, pyridine, and the like. It will be recognized that the saturated or unsaturated 5-, 6- or 7-membered ring may optionally have one or more additional heteroatoms in the ring.

The term "heterocyclic" is used herein at all occurrences to mean a saturated or wholly or partially unsaturated 5–10-membered ring system (unless the cyclic ring system is otherwise limited) in which one or more rings contain one or more heteroatoms, including, but not limited to, pyrrolidine, piperidine, piperazine, morpholine, imidazolidine, pyrazolidine, and the like.

The term "CCR5 mediated disease state" is used herein at all occurrences to mean any disease state which is mediated (or modulated) by CCR5.

Suitably, pharmaceutically acceptable salts of formula (I) include, but are not limited to, salts with inorganic acids such as hydrochloride, sulfate, phosphate, diphosphate, hydrobromide, and nitrate, or salts with an organic acid such as malate, maleate, fumarate, tartrate, succinate, citrate, acetate, lactate, methanesulfonate, p-toluenesulfonate, palmitate, salicylate, and stearate.

Among the preferred compounds of the invention are the following compounds:

N-[3-(2-Dimethylamino)ethoxy-4-methoxyphenyl]-2'-methyl-4'-(5-methyl-1,2,4-oxadiazol-3-yl)-(1,1'-biphenyl)-4-carboxamide;

N-[3-(2-Methylamino)ethoxy-4-methoxyphenyl]-2'-methyl-4'-(5-methyl-1,2,4-oxadiazol-3-yl)-(1,1'-biphenyl)-4-carboxamide;

N-[3-(2-Amino)ethoxy-4-methoxyphenyl]-2'-methyl-4'-(5-methyl-1,2,4-oxadiazol-3-yl)-(1',1'-biphenyl)-4-carboxamide;

N-[3-(2-Dimethylamino-1-methyl)ethoxy-4-methoxyphenyl]-2'-methyl-4'-(5-methyl-1,2,4-oxadiazol-3-yl)-(1,1'-biphenyl)-4-carboxamide;

3-(2-Dimethylaminoethoxy)-4-methoxy-N-[2'-methyl-4'-(5-methyl-1,2,4-oxadiazol-3-yl)[1,1'-biphenyl]]-4-benzamide oxalate;

N-[3-(2-Diethylamino)ethoxy-4-methoxyphenyl]-2'-methyl-4'-(5-methyl-1,2,4-oxadiazol-3-yl)-(1,1-biphenyl)-4-carboxamide oxalate;

N-[3-(2-Dimethylaminoethoxy)-4-methoxyphenyl]-4'-(5-ethyl-1,2,4-oxadiazol-3-yl)-2'-methylbiphenyl-4-carboxamide;

N-[3-(2-Pyrrolidin-1-ylethoxy)-4-methoxyphenyl]-4'-(5-methyl-1,2,4-oxadiazol-3-yl)-2'-methylbiphenyl-4-carboxamide;

N-[3-(2-Dimethylamino)ethoxy-4-methoxyphenyl-2'-ethyl-4'-(5-methyl-1,2,4-oxadiazol-3-yl)-(1,1'-biphenyl)-4-carboxamide hydrochloride;

N-(3-(2-Dimethylamino)ethoxy-4-methoxyphenyl)-2',3-dimethyl-4'-(5-methyl-1,2,4-oxadiazol-3-yl)-1,1'-biphenyl-4-carboxamide hydrochloride;

N-[3-((S)-1-Methylpyrrolidin-2-ylmethoxy)-4-methoxyphenyl]-4'-(5-methyl-1,2,4-oxadiazol-3-yl)-2'-methyl-biphenyl-4-carboxamide;

N-[3-(1-Methyl-3-piperidinyloxy)-4-methoxyphenyl]-4'-(5-methyl-1,2,4-oxadiazol-3-yl)-2'-methyl-biphenyl-4-carboxamide oxalate;

N-[3-(1-Methyl-3-azepinyloxy)-4-methoxyphenyl]-4'-(5-methyl-1,2,4-oxadiazol-3-yl)-2'-methyl-biphenyl-4-carboxamide oxalate;

N-[4-Methoxy-3-(quinuclidine-3-yloxy)phenyl]-2'-methyl-4'-(5-methyl-1,2,4-oxadiazol-3-yl)biphenyl-4-carboxamide oxalate;

N-[3-((R)-1-Methylpyrrolidin-2-ylmethoxy)-4-methoxyphenyl]-4'-(5-methyl-1,2,4-oxadiazol-3-yl)-2'-methyl-biphenyl-4-carboxamide;

N-[3-(1-Methylpyrrolidin-3-yl)-4-methoxy-phenyl]-4'-(5-methyl-1,2,4-oxadiazol-3-yl)-2'-methyl-biphenyl-4-carboxamide;

N-[3-((R)-Pyrrolidin-2-ylmethoxy)-4-methoxyphenyl]-4'-(5-methyl-1,2,4-oxadiazol-3-yl)-2'-methylbiphenyl-4-carboxamide hydrochloride;

N-[3-(Azetidin-2-ylmethoxy)-4-methoxyphenyl]-4'-(5-methyl-1,2,4-oxadiazol-3-yl)-2'-methylbiphenyl-4-carboxamide hydrochloride;

N-[2-(Dimethylaminomethyl)1,4-benzodioxan-7-yl]-2'-methyl-4'-(5-methyl-1,2,4-oxadiazol-3-yl)biphenyl-4-carboxamide;

N-[2-(dimethylaminomethyl)-1,4-benzodioxan-6-yl]-2'-methyl-4'-(5-methyl-1,2,4-oxadiazol-3-yl)biphenyl-4-carboxamide;

2,3-Dihydro-6-(2-dimethylaminoethoxy)-5-methoxy-1-[4-(2-methyl-4-(5-methyl-1,2,4-oxadiazol-3-yl)phenyl)benzoyl]indole;

6-(2-Dimethylamiinoethoxy)-5-methoxy-1-[4-(2-methyl-4-(5-methyl-1,2,4-oxadiazol-3-yl)phenyl)benzoyl]indole;

2,3-Dihydro-6-(2-dimethylaminoethoxy)-5-methoxy-2-methyl-1-[4-(2-methyl-4-(5-methyl-1,2,4-oxadiazol-3-yl)phenyl)benzoyl]indole oxalate;

6-(2-Dimethylaminoethoxy)-5-methoxy-2-methyl-1-[4-(2-methyl-4-(5-methyl-1,2,4-oxadiazol-3-yl)phenyl)benzoyl]indole oxalate;

[7-(2-Dimethylaminoethoxy)-6-methoxy-2-methyl-3,4-dihydro-2H-quinolin-1-yl][2'-methyl-4'-(5-methyl-1,2,4-oxadiazol-3-yl)-biphenyl-4-yl]methanone oxalate;

[8-(2-Dimethylaminoethoxy)-7-methoxy-2,3,4,5-tetrahydro-1H-benz[b]azepin-1-yl]-[2'-methyl-4'-(5-methyl-1,2,4-oxadiazol-3-yl)-biphenyl-4-yl]methanone oxalate;

5-[4-(2-Methyl-4-(5-methyl-1,2,4-oxadiazol-3-yl)phenyl)-benzoylamino]spiro[(2,3-dihydrobenzofuran)-3,4'-piperidine]hydrochloride;

2,3,6,7-Tetrahydro-1'-methyl-5-[2'-methyl-4'-(5-methyl-1,2,4-oxadiazol-3-yl)biphenyl-4-carbonyl]furo[2,3-f]indole-3-spiro-4'-piperidine hydrochloride;

5-[4'-(5-Dimethylamino-1,2,4-oxadiazol-3-yl)-2'-methylbiphenyl-4-carbonyl]-1'-methyl-2,3,5,6,7,8-hexahydrospiro(furo[2,3-g]quinoline-3,4'-piperidine) hydrochloride;

5-[4'-(5-Hydroxymethyl-1,2,4-oxadiazol-3-yl)-2'-methylbiphenyl-4-carbonyl]-1'-methyl-2,3,6,7-tetrahydrospiro[furo[2,3-f]indole-3,4'-piperidine] hydrochloride;

5-[4'-(5-Methoxymethyl-1,2,4-oxadiazol-3-yl)-2'-methylbiphenyl-4-carbonyl]-1'-methyl-2,3,6,7-tetrahydrospiro[furo[2,3-f]indole]-3-4'-piperidine hydrochloride;

4'-ax-(Dimethylamino)-5-[2'-methyl-4'-[(5-methyl-1,2,4-oxadiazol-3-yl)biphenyl-4-yl]carbonyl]-2,3,6,7-tetrahydrospiro[furo[2,3-f]indole-3,1'-cyclohexane] hydrochloride.

N-[3-(2-Dimethylamino)ethoxy-phenyl]-[1,1'-biphenyl]-4-carboxamide;

N-[4-(2-Dimethylamino)ethoxy-phenyl]-[1,1'-biphenyl]-4-carboxamide;

N-[2-(3-Dimethylamino)propoxy-phenyl]-[1,1'-biphenyl]-4-carboxamide;

N-[3-[2-(Morpholin-1-yl)ethoxy]-4-methoxyphenyl]-[1,1'-biphenyl]-4-carboxamide;

N-[3-(2-Dicyclohexylamino)ethoxy-4-methoxyphenyl]-[1,1'-biphenyl]-4-carboxamide;

N-Ethyl-N-[3-[2-(N-isopropyl-N-methylamino)ethoxy]-4-methoxyphenyl]-1,1'-biphenyl-4-carboxamide;

N-Methyl-N-[3-(2-diisopropylamino)ethoxy-4-methoxyphenyl]-2'-methyl-4'-(5-methyl-1,2,4-oxadiazol-3-yl)-(1,1-biphenyl)-4-carboxamide;

N-Methyl-N-[3-(diisopropylamino)ethoxy-4-methoxyphenyl]-[1,1'-biphenyl]-4-carboxamide;

N-[3-(2-Diisopropylamino)ethoxy-4-methoxyphenyl]-4-iodobenzamide;

N-[3-(2-Diisopropylamino)ethoxy-4-methoxyphenyl]-3-bromobenzamide;

N-[3-(2-Diisopropylamino)ethoxy-4-methoxyphenyl]-4-(methoxy)benzamide;

N-[4-(2-Diisopropylamino)ethoxy-phenyl]-4-iodobenzamide;

N-[3-(2-Diethylamino)ethoxy-4-methoxyphenyl]-3-iodobenzamide;

N-[3-(2-Diisopropylamino)ethoxy-phenyl]-3-iodobenzamide;

N-[3-(2-Diethylamino)ethoxy-phenyl]-3-iodobenzamide;

N-[3-(2-Diethylamino)ethoxy-4-methoxyphenyl]-4-bromobenzamide;

N-[4-(2-Diisopropylamino)ethoxy-phenyl]-4-bromobenzamide;

N-[3-(2-Diethylamino)ethoxy-4-methoxyphenyl]-3-bromobenzamide;

N-[4-(2-Diisopropylamino)ethoxy-phenyl]-4-(isopropyl)benzamide;

N-[3-(2-Diethylamino)ethoxy-4-methoxyphenyl]-4-(cyclohexyl)benzamide;

N-[4-(2-Diethylamino)ethoxy-phenyl]-4-(cyclohexyl)benzamide;

N-[4-(2-Diisopropylamino)ethoxy-phenyl]-4'-ethyl-[1,1'-biphenyl]-4-carboxamide;

N-[4-(2-Diethylamino)ethoxy-phenyl]-4'-ethyl-[1,1'-biphenyl]-4-carboxamide;

N-[3-(2-Dimethylamino)ethoxy-4-methoxyphenyl]-4'-methoxy-[1,1'-biphenyl]-4-carboxamide;

N-[3-(2-Dimethylamino)ethoxy-4-methoxyphenyl]-4'-hydroxy-[1,1'-biphenyl]-4-carboxamide;

N-[3-(2-Dimethylamino)ethoxy-4-methoxyphenyl]-3'-hydroxy-[1,1'-biphenyl]-4-carboxamide;

N-[2-(dimethylaminomethyl)-1,4-benzodioxan-7-yl]-2'-methyl-4'-(5-methyl-1,2,4-oxadiazol-3-yl)biphenyl-4-carboxamide; and N-[2-(dimethylaminomethyl)-1,4-benzodioxan-6-yl]-2'-methyl-4'-(5-methyl-1,2,4-oxadiazol-3-yl)biphenyl-4-carboxamide.

Among the more preferred compounds of the invention are the following compounds:

N-[3-(3-Dimethylamino)propoxy-4-methoxyphenyl]-2'-methyl-4'-(5-methyl-1,2,4-oxadiazol-3-yl)-(1,1'-biphenyl)-4-carboxamide;

N-[3-(2-Piperidine)ethoxy-4-methoxyphenyl]-2'-methyl-4'-(5-methyl-1,2,4-oxadiazol-3-yl)-(1,1'biphenyl)-4-carboxamide;
N-[3-(3-Dimethylaminopropyl)-4-methoxyphenyl]-2'-methyl-4'-(5-methyl-1,2,4-oxadiazol-3-yl)biphenyl-4-carboxamide oxalate;
N-[3-(1-Methyl-4-piperidyl)-4-methoxyphenyl]-2'-methyl-4'-(5-methyl-1,2,4-oxadiazol-3-yl)biphenyl-4-carboxamide oxalate;
N-[3-(1-Methyl-3-piperidyl)methoxyphenyl]-2'-methyl-4'-(5-methyl-1,2,4-oxadiazol-3-yl)biphenyl-4-carboxamide oxalate;
N-[7-(2-Dimethylamino)ethoxy-2,3-dihydrobenzofuran-5-yl]-2'-methyl-4'-(5-methyl-1,2,4-oxadiazol-3-yl)-1,1'-biphenyl-4-carboxamide;
[3-(Dimethylaminoethyl)-3,6,7,8-tetrahydro-2H-furo[2,3-g]quinolin-5-yl]-[2'-methyl-4'-(5-methyl-[1,2,4]-oxadiazol-3-yl)-biphenyl-4-yl]-methanone oxalate;
5-[4-(2-Methyl-4-(5-methyl-1,2,4-oxadiazol-3-yl)phenyl)benzoylamino]-spiro[(2,3-dihydrobenzofuran)-3,4'-(1-methylhexahydroazepine)]oxalate;
2,3,5,6,7,8,-Hexahydro-1'-methyl-5-{2'-methyl-4'-[(5-methyl-1,2,4-oxadiazol-3-yl)biphenyl-4-yl]carbonyl}furo[2,3-g]quinoline-3-spiro-4'piperidine oxalate;
6,7,8,9-Tetrahydro-1'-methyl-5-[[2'-methyl-4'-(5-methyl-1,2,4-oxadiazol-3-yl)[1,1'-biphenyl]-4-yl]carbonyl]-spiro[2H-furo[2,3-h][1]benzazepine-3(5H),4'-piperidine];
2,3,5,6,7,8-Hexahydro-5-[4'-(5-hydroxymethyl-1,2,4-oxadiazol-3-yl)-2'-methylbiphenyl-4-carbonyl]-1'-methylspiro[furo[2,3-g]quinoline-3,4'-piperidine] hydrochloride;
4'-(Dimethylamino)-5-[2'-methyl-4'-[(5-methyl-1,2,4-oxadiazol-3-yl)-biphenyl-4-yl]carbonyl]-2,3,6,7-tetrahydrospiro[furo[2,3-f]indole-3,1'-cyclohexane] hydrochloride;
N-[3-(2-Diisopropylamino)ethoxy-4-methoxyphenyl]-[1,1'-biphenyl]-3-carboxamide;
N-[3-(3-Dimethylamino)propoxy-phenyl]-[1,1'-biphenyl]-4-carboxamide;
N-[4-(3-Dimethylamino)propoxy-phenyl]-[1,1'-biphenyl]-4-carboxamide;
N-[3-(Diethylamino)ethoxy-4-methoxyphenyl]-[1,1'-biphenyl]-4-carboxamide;
N-[3-[2-(Piperidin-1-yl)ethoxy]-4-methoxyphenyl]-[1,1'-biphenyl]-4-carboxamide;
N-[3-(2-Diisopropylamino)ethoxy-2-methylphenyl]-2'-methyl-4'-(5-methyl-1,2,4-oxadiazol-3-yl)-[1,1'-biphenyl]-4-carboxamide;
N-[3-(2-Dipropylamino)ethoxy-4-methoxyphenyl]-[1,1'-biphenyl]-4-carboxamide;
N-[3-(2-Diisopropylamino)ethoxy-4-methylphenyl]-[1,1'-biphenyl]-4-carboxamide;
N-[3-(2-Diisopropylamino)ethoxy-4-ethylphenyl]-[1,1'-biphenyl]-4-carboxamide;
N-[3-(2-Diisopropylamino)ethoxy-4-(methoxycarbonylamino)phenyl]-[1,1'-biphenyl]-4-carboxamide;
N-[1,1'-Biphenyl]-4-yl-3-(2-diisopropylamino)ethoxy-4-methoxybenzamide;
N-[3-(2-Diisopropylamino)ethoxy-4-(ethoxycarbonyl)phenyl]-[1,1'-biphenyl]-4-carboxamide;
N-[4-(2-Diisopropylamino)ethoxy-3-methoxyphenyl]-[1,1'-biphenyl]-4-carboxamide;
N-[2-(2-Diisopropylamino)ethoxy-4-methoxyphenyl)-[1,1'-biphenyl]-4-carboxamide;
N-[3-(2-diisopropylamino)ethoxy-phenyl]-[1,1'-biphenyl]-4-carboxamide;
N-[2-Fluoro-4-(2-diisopropylamino)ethoxy-phenyl]-[1,1'-biphenyl]-4-carboxamide;
N-[4-(2-Diisopropylamino)ethoxy-phenyl]-[1,1'-biphenyl]-4-carboxamide;
N-[2-(2-Diisopropylamino)ethoxy-phenyl]-[1,1'-biphenyl]-4-carboxamide;
N-[3-(2-Diisopropylamino)ethoxy-4-methoxyphenyl]-4-bromobenzamide;
N-[3-(2-Diisopropylamino)ethoxy-4-methoxyphenyl]-4-(isopropyl)benzamide;
N-[3-(2-Diisopropylamino)ethoxy-4-methoxyphenyl]-4-(cyclohexyl)benzamide;
N-[3-(2-Diisopropylamino)ethoxy-4-methoxyphenyl]-3,4-dichlorobenzamide;
N-[3-(2-Diisopropylamino)ethoxy-4-methoxyphenyl]-3,5-dichlororbenzamide;
N-[3-(2-Diisopropylamino)ethoxy-4-methoxyphenyl]-4-(nitro)benzamide;
N-[3-(2-Diisopropylamino)ethoxy-4-methoxyphenyl]-3-iodobenzamide;
N-[4-(2-Diisopropylamino)ethoxy-phenyl]-3-iodobenzamide;
N-[4-(2-Diisopropylamino)ethoxy-phenyl]-3-bromobenzamide;
N-[4-(2-Diisopropylamino)ethoxy-phenyl]-4-(cyclohexyl)benzamide;
N-[3-(2-Diisopropylamino)ethoxy-4-methoxy-phenyl]-4-(cyclohexyl)benzamide;
N-[3-(2-Diethylamino)ethoxy-4-methoxyphenyl]-4'-ethyl-[1,1'-biphenyl]-4-carboxamide;
N-[3-(2-Diisopropylamino)ethoxy-phenyl]-4'-ethyl-[1,1'-biphenyl]-4-carboxamide; and
N-[3-(2-Dimethylamino)ethoxy-4-methoxyphenyl]-3'-methoxy-[1,1'-biphenyl]-4-carboxamide).

Among the most preferred compounds of the invention are the following compounds:

N-[3-(2-Diisopropylamino)ethoxy-phenyl]-2'-methyl-4'-(5-methyl-1,2,4-oxadiazol-3-yl)-(1,1'-biphenyl)-4-carboxamide;
N-[3-(2-Diisopropylamino)ethoxy-4-methoxyphenyl]-2'-methyl-4'-(5-methyl-1,2,4-oxadiazol-3-yl)-(1,1'-biphenyl)-4-carboxamide;
5-[4-(2-methyl-4-(5-methyl-1,2,4-oxadiazol-3-yl)phenyl)benzoylamino]spiro[(2,3-dihydrobenzofuran)-3,4'-(1-methylpiperidine)]oxalate;
N-[3-(2-Diisopropylamino)ethoxy-4-methoxyphenyl]-(1,1'-biphenyl)-4-carboxamide;
N-[3-(2-Diisopropylamino)ethoxy-4-methoxyphenyl]-2'-methyl-(1,1'-biphenyl)-4-carboxamide;
N-[3-(2-Diisopropylamino)ethoxy-phenyl]-2'-methyl-4'-(5-methyl-1,2,4-oxadiazol-3-yl)-[1,1'-biphenyl]-4-carboxamide;
N-[3-[2-(N-Cyclohexyl-N-isopropylamino)ethoxy]-4-methoxyphenyl]-[1,1'-biphenyl]-carboxamide;
N-[3-[2-(cis-2,6-Dimethylpiperidin-1-yl)ethoxy]-4-methoxyphenyl]-[1,1'-biphenyl]-4-carboxamide;
N-[3-[2-(N-Ethyl-N-isopropyl amino)ethoxy]-4-methoxyphenyl]-[1,1'-biphenyl]-4-carboxamide;
N-[3-[2-(2,5-Dimethypyrrolidin-1-yl)ethoxy]-4-methoxyphenyl]-[1,1'-biphenyl]-4-carboxamide;
N-[4-Methoxy-3-[2-(2,2,6,6-tetramethylpiperidin-1-yl)ethoxy]phenyl]-1,1'-biphenyl-4-carboxamide;
N-[3-[2-(N-t-Butyl-N-isopropyl)aminoethoxy]-4-methoxyphenyl]-[1,1'-biphenyl]-4-carboxamide;
N-[3-(3-Diisopropylamino)propyloxy-4-methoxyphenyl]-[1,1'-biphenyl]-4-carboxamide;

N-[3-(3-Diisopropylamino)propyl-4-methoxyphenyl]-[1,1'-biphenyl]-4-carboxamide;
N-[3-(2-Diisopropylamino)ethoxy-4-iodophenyl-[1,1'-biphenyl]-4-carboxamide;
N-[3-(2-Diisopropylamino)ethoxy-4-methoxyphenyl]-[1,1'-biphenyl]-4-methanamine Dihydrochloride;
N-[3-(2-Diisopropylamino)ethoxy-4-methoxy-phenyl]-4'-cyano-1,1'-biphenyl-4-carboxamide;
N-[3-(2-Diisopropylamino)ethoxy-4-methoxyphenyl]-4'-cyano-2'-methyl-1,1'-biphenyl-4-carboxamide;
N-[3-(2-Diisopropylamino)ethoxy-4-methoxyphenyl]-2-naphthalenecarboxamide;
N-(1'-Methylspiro[benzofuran-3(2H),4'-piperidin]-5-yl-[1,1'-biphenyl]-4-carboxamide;
N-[3-[2-(N-Isopropyl-N-methylamino)ethoxy]-4-methoxyphenyl]-[1,1'-biphenyl]-4-carboxamide;
N-[3-(2-Diisopropylamino)ethoxy-4-methoxyphenyl]-4-(iodo)benzamide;
N-[3-(2-Diisopropylamino)ethoxy-4-methoxy-phenyl]-4-(cyclohexyl)benzamide;
N-[3-(2-Diisopropylamino)ethoxy-4-methoxyphenyl]-4'-ethyl-[1,1'-biphenyl]-4-carboxamide;
N-[3-(2-Diisopropylamino)ethoxy-4-methoxyphenyl]-3'-methoxy-[1,1'-biphenyl]-4-carboxamide;
N-[3-(2-Diisopropylamino)ethoxy-4-methoxyphenyl]-4'-acetyl-[1,1'-biphenyl]-4-carboxamide;
N-[3-(2-Diethylamino)ethoxy-4-methoxyphenyl]-3'-methoxy-[1,1'-biphenyl]-4-carboxamide; and
N-[3-(2-Diisopropylamino)ethoxy-4-methoxyphenyl]-3'-hydroxy-[1,1'-biphenyl]-4-carboxamide.

Compounds excluded from the scope of this invention are as follows:

N-[3-(2-Dimethylaminoethoxy)-4-methoxyphenyl]-4'-(5-dimethylamino-1,2,4-oxadiazol-3-yl)-2'-methylbiphenyl-4-carboxamide;
N-[3-(1-Methylazetidin-2-ylmethoxy)-4-methoxyphenyl]-4'-(5-methyl-1,2,4-oxadiazol-3-yl)-2'-methylbiphenyl-4-carboxamide;
[7-(2-Dimethylaminoethoxy)-6-methoxy-3,4-dihydro-2H-quinolin-1-yl]-[2'-methyl-[1,2,4]-oxadiazol-3-yl)biphenyl-4-yl]-methanone oxalate;
2,3,6,7-Tetrahydro-1'-methyl-5-[2'-methyl-4'-(5-methyl-1,2,4-oxadiazol-3-yl)biphenyl-4-carbonyl]-furo[2,3-f]indole-3-spiro-3'-piperidine oxalate;
5-[4'-(5-Methyl-1,2,4-oxadiazol-3-yl)biphenyl-4-carbonyl]-1'-methyl-2,3,6,7-tetrahydrofuro[2,3-f]indole-3-spiro-4'-piperidine;
1'-Ethyl-5-[2'-methyl-4'-(5-methyl-1,2,4-oxadiazol-3-yl)-biphenyl-4-carbonyl]-2,3,6,7-tetrahydrospirofuro[2,3-f]indole-3,4'-piperidine;
N-[2-(2-Dimethylamino)ethoxy-phenyl]-[1,1'-biphenyl]-4-carboxamide;
N-[3-(2-Diisopropylamino)ethoxy-4-methoxyphenyl] benzamide;
N-[3-(2-Diisopropylamino)ethoxy-4-methoxyphenyl]-[1,1'-biphenyl]-2-carboxamide;
N-[3-(2-Diethylamino)ethoxy-4-methoxyphenyl]-4-(methoxy)benzamide;
N-[3-(2-Diethylamino)ethoxy-4-methoxyphenyl]-4-(nitro)benzamide;
N-[3-(2-Diethylamino)ethoxy-4-methoxyphenyl]-4-(nitro)benzamide;
N-[3-(2-Dimethylamino)ethoxy-4-methoxyphenyl]-4-(nitro)benzamide;
N-[3-(Dimethylamino)ethoxy-4-methoxyphenyl]-[1,1'-biphenyl]-4-carboxamide;
N-[3-(2-Dimethylamino)ethoxy-4-methoxyphenyl]-4'-chloro-[1,1'-biphenyl]-4-carboxamide;
N-[3-(2-Diethylamino)ethoxy-4-methoxyphenyl]-4'-hydroxy-[1,1'-biphenyl]-4-carboxamide;
N-[3-(2-Diethylamino)ethoxy-4-methoxyphenyl]-4'-acetyl-[1,1'-biphenyl]-4-carboxamide;
N-[3-(2-Dimethylamino)ethoxy-4-methoxyphenyl]-4'-acetyl-[1,1'-biphenyl]-4-carboxamide;
N-[3-(2-Dimethylamino)ethoxy-4-methoxyphenyl]-3'-chloro-[1,1'-biphenyl]-4-carboxamide;
N-[3-(2-Diethylamino)ethoxy-4-methoxyphenyl]-3'-nitro-[1,1'-biphenyl]-4-carboxamide;
N-[3-(2-Dimethylamino)ethoxy-4-methoxyphenyl]-3'-nitro-[1,1'-biphenyl]-4-carboxamide;
N-[3-(2-Diethylamino)ethoxy-4-methoxyphenyl]-4-iodobenzamide;
N-[4-(2-Diethylamino)ethoxy-phenyl]-4-iodobenzamide;
N-[2-(2-Diisopropylamino)ethoxy-phenyl]-4-iodobenzamide;
N-[4-(2-Diethylamino)ethoxy-phenyl-3-iodobenzamide;
N-[2-(2-Diisopropylamino)ethoxy-phenyl]-3-iodobenzamide;
N-[2-(2-Diethylamino)ethoxy-phenyl]-3-iodobenzamide;
N-[3-(2-Diethylamino)ethoxy-phenyl]-4-bromobenzamide;
N-[2-(2-Diisopropylamino)ethoxy-phenyl]-4-bromobenzamide;
N-[2-(2-Diethylamino)ethoxy-phenyl]-4-bromobenzamide;
N-[4-(2-Diethylamino)ethoxy-phenyl]-3-bromobenzamide;
N-[2-(2-Diisopropylamino)ethoxy-phenyl]-3-bromobenzamide;
N-[2-(2-Diethylamino)ethoxy-phenyl]-3-bromobenzamide;
N-[3-(2-Diethylamino)ethoxy-4-methoxyphenyl]-4-(dimethylamino)benzamide;
N-[4-(2-Diisopropylamino)ethoxy-phenyl]-4-(dimethylamino)benzamide;
N-[4-(2-Diethylamino)ethoxy-phenyl]-4-(dimethylamino)benzamide;
N-[2-(2-Diisopropylamino)ethoxy-phenyl]-4-(dimethylamino)benzamide;
N-[2-(2-Diethylamino)ethoxy-phenyl]-4-(dimethylamino)benzamide;
N-[4-(2-Diethylamino)ethoxy-phenyl]-4-(isopropyl)benzamide;
N-[2-(2-Diisopropylamino)ethoxy-phenyl]-4-(isopropyl)benzamide;
N-[2-(2-Diethylamino)ethoxy-phenyl]-4-(isopropyl)benzamide;
N-[3-(2-Diethylamino)ethoxy-phenyl]-4-(cyclohexyl)benzamide;
N-[2-(2-Diisopropylamino)ethoxy-phenyl]-4-(cyclohexyl)benzamide;
N-[2-(2-Diethylamino)ethoxy-phenyl]-4-(cyclohexyl)benzamide;
N-[2-(2-Diisopropylamino)ethoxy-phenyl]-4'-ethyl-[1,1'-biphenyl]-4-carboxamide; and
N-[2-(2-Diethylamino)ethoxy-phenyl]-4'-ethyl-[1,1'-biphenyl]-4-carboxamide.

Formulation of Pharmaceutical Compositions

The pharmaceutically effective compounds of this invention (and the pharmaceutically acceptable salts thereof) are administered in conventional dosage forms prepared by combining a compound of formula (I) ("active ingredient") in an amount sufficient to treat COPD, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, inflammatory bowel disease, and HIV infection, ("CCR5-mediated disease states") with standard pharmaceutical carriers or diluents according to conventional procedures well known in the art. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1000 mg. When a liquid carrier is used, the preparation will be in the form of a syrup, emulsion, soft gelatin capsule, sterile injectable liquid such as an ampule or nonaqueous liquid suspension.

The active ingredient may also be administered topically to a mammal in need of treatment or prophylaxis of CCR5 mediated disease states. The amount of active ingredient required for therapeutic effect on topical administration will, of course, vary with the compound chosen, the nature and severity of the disease state being treated and the mammal undergoing treatment, and is ultimately at the discretion of the physician. A suitable dose of an active ingredient is 1.5 mg to 500 mg for topical administration, the most preferred dosage being 1 mg to 100 mg, for example 5 to 25 mg administered two or three times daily.

By topical administration is meant non-systemic administration and includes the application of the active ingredient externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous or alcoholic solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol. The formulation may incorporate any suitable surface active agent such as an anionic, cationic or non-ionic surfactant such as esters or polyoxyethylene derivatives thereof. Suspending agents such as natural gums, cellulose derivatives or inorganic materials such as siliceous silicas, and other ingredients such as lanolin, may also be included.

The active ingredient may also be administered by inhalation. By "inhalation" is meant intranasal and oral inhalation administration. Appropriate dosage forms for such administration, such as an aerosol formulation or a metered dose inhaler, may be prepared by conventional techniques. The daily dosage amount of the active ingredient administered by inhalation is from about 0.1 mg to about 100 mg per day, preferably about 1 mg to about 10 mg per day.

In one aspect, this invention relates to a method of treating COPD, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, inflammatory bowel disease, and HIV infection, all in mammals, preferably humans, which comprises administering to such mammal an effective amount of a CCR5 receptor ligand, in particular, a compound as depicted in formula (I).

By the term "treating" is meant either prophylactic or therapeutic therapy. Such formula (I) compound can be administered to such mammal in a conventional dosage form prepared by combining the formula (I) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. The formula (I) compound is administered to a mammal in need of treatment for asthma and atopic disorders (for example, atopic dermatitis and allergies), rheumatoid arthritis, atherosclerosis, psoriasis, autoimmune diseases such as multiple sclerosis, inflammatory bowel disease, and HIV infection, in an amount sufficient to decrease symptoms associated with these disease states. The route of administration may be oral or parenteral.

The term parenteral as used herein includes intravenous, intramuscular, subcutaneous, intra-rectal, intravaginal or intraperitoneal administration. The subcutaneous and intramuscular forms of parenteral administration are generally preferred. The daily parenteral dosage regimen will preferably be from about 30 mg to about 300 mg per day of active ingredient. The daily oral dosage regimen will preferably be from about 100 mg to about 2000 mg per day of active ingredient.

It will be recognized by one of skill in the art that the optimal quantity and spacing of individual dosages of a formula (I) compound will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of the formula (I) compound given per day for a defined number of days, can be ascertained by those skilled in the art using conventional course of treatment determination tests.

Methods of Preparation

The compounds of formula (I) can be prepared by art-recognized procedures from known or commercially available starting materials. If the starting materials are unavailable from a commercial source, their synthesis is described herein, or they can be prepared by procedures known in the art.

Specifically, compounds of formula (I) wherein R is represented by group (a), A is CONH and E is represented by group (d), were prepared according to the methods of international application publication number WO 95/15954, published Jun. 15, 1995.

Compounds of formula (I) wherein R is represented by group (a), A is CONH and E is represented by group (e), were prepared according to the methods of international application publication number WO 95/17401, published Jun. 29, 1995.

Compounds of formula (I) wherein R is represented by group (a), A is CONH and E is represented by group (f), were prepared according the methods of international application publication number WO 96/31508 published Oct. 10, 1996.

Compounds of formula (I) wherein R is represented by group (a), A is CONH and E is represented by groups (g) or (h), were prepared according the methods of international application publication number WO 95/30675, published Nov. 16, 1995.

Compounds of formula (I) wherein R is represented by group (a), A is CONH and E is represented by group (j), were prepared according the methods of international application publication number WO 96/11934, published Apr. 25, 1996.

Compounds of formula (I) wherein R is represented by group (a) and AE is represented by group (k), were prepared according the methods of international application publication number WO 95/17398, published Jun. 29, 1995.

Compounds of formula (I) wherein R is represented by group (a) and AE is represented by group (l), were prepared according the methods of international application publication number WO 97/07120, published Feb. 27, 1997.

Compounds of formula (I) wherein R is represented by group (a) and AE is represented by group (m), were prepared according the methods of international application publication number WO 96/19477, published Jun. 27, 1996.

Compounds of formula (I) wherein R is represented by group (a) and AE is represented by group (n), were prepared according the methods of international application publication number WO 97/19070 published May 29, 1997.

Specifically, compounds of formula (I) wherein Ar is represented by group (i), (ii) or (iii), A is $CONR^{46}$, NHCO or $CH_2NH$, and E is represented by group (a), were prepared according to the methods of international application publication number WO 95/15954, published Jun. 15, 1995, international application publication number WO 95/17398, published Jun. 29, 1995, international application publication number WO 95/263284, published Oct. 5, 1995, international application publication number WO 96/06079, published Feb. 29, 1996, GB 2276161 published Sep. 21, 1994, and GB 2276165 published Sep. 21, 1994.

Compounds of formula (I) wherein Ar is (i) or (ii), and A is $CONR^{60}$ or NHCO, and E is represented by group (b), were prepared according to the methods of international application publication number WO 95/11934, published Apr. 25, 1995, and WO 95/19477, published Jun. 27, 1995. Four other applications cover the spiro compounds WO 97/17350 published May 15, 1997; WO 97/34900 published Sep. 25, 1997; WO 97/34901 published Sep. 25, 1997; WO 97/35862 published Oct. 2, 1997.

Compounds of formula (I) wherein Ar is (i), (ii) or (iii), A is $CONR^{70}$, NHCO or $CH_2NH$, and E represents (c), were prepared according the methods of international application publication number WO 95/306758 published Nov. 16, 1995 and GB 2276165 published Sep. 21, 1994.

Compounds of formula (I) wherein Ar is (ii), A is CONH or NHCO, and E represents (f), were prepared according the methods of international application publication number WO 95/17401, published Jun. 29, 1995.

Compounds of formula (I) wherein Ar is (i) or (ii), A is $CONR^{93}$, and E represents a group (g), were prepared according the methods of international application publication number WO 96/31508, published Oct. 10, 1996.

Compounds of formula (I) when Ar is (i) or (ii), A is $CONR^{101}$, and E represents group (h), were prepared according the methods of international application publication number WO 95/32767, published Dec. 7, 1995 and WO 97/07120, published Feb. 27, 1997.

Compounds of formula (I) Ar is (i) or (ii), and A is $CONR^{109}$ or $CH_2NH$, and E represents group (i), were prepared according the methods of international application publication number WO 97/19070, published May 29, 1997.

Compounds of formula (I) are also prepared by the method of Scheme 1 using solid-phase chemistry. Resin 1-1 (WO 98/17695) is coupled with a suitably substituted carboxyphenyl-boronic acid, for Example 4-(4,4,5,5-tetramethyl-1,3,2-dioxaborolan-2-yl)benzoic acid, using Suzuki conditions, for example, a suitable palladium reagent, such as tetrakis(triphenylphosphine)palladium(0), and a suitable base, such as sodium carbonate, in a suitable solvent, such as ethanol and toluene, at a suitable temperature, such as 90° C., for a suitable time, such as 24 h, to afford the resin-bound biphenylcarboxylic acid 1-2. The adduct 1-2 is condensed with appropriately substituted anilines 1-4, prepared by methods known to the art from commercially available starting materials or as described herein, using methods known to the art. For example, treatment of 1-2 with a suitable reagent, such as oxalyl chloride, in a suitable solvent, such as toluene, affords the biphenylcarbonyl chloride adduct 1-3. Treatment of 1-3 with 1-4 in a suitable solvent, such as dichloromethane, in the presence of a suitable base, such as diisopropylethylamine, gives the biphenylcarboxanilide adduct, 1-5. Treatment of 1-5 with a suitable acid and solvent, such as trifluoroacetic/dichloromethane/water (50:48:2) affords 1-6 which are compounds of formula (I).

Compounds of formula (I) are also prepared by the method of Scheme 2 using solid-phase chemistry. Appropriately substituted (alkylamino)ethoxy-anilines 2-1, such as 3-(2-diisopropylamino)-ethoxy-4-methoxyaniline, synthesized according to literature methods from commercially available starting materials and by methods described herein, are reacted with 4-formyl-3,5-dimethoxyphenol-Merrifield resin 2-2 (Boojamra, et al., *J. Org. Chem.* 1995, 60, 5742) is treated and a suitable reducing agent, such as sodium triacetoxyborohydride, in a suitable solvent, such as dimethylformamide containing 1% acetic acid, to afford 2-3. The resin-bound aniline 2-3 is condensed with an appropriately substituted benzoic acid or biphenylcarboxylic acid, which are commercially available or synthesized by methods known to the art, using a suitable activating agent, such

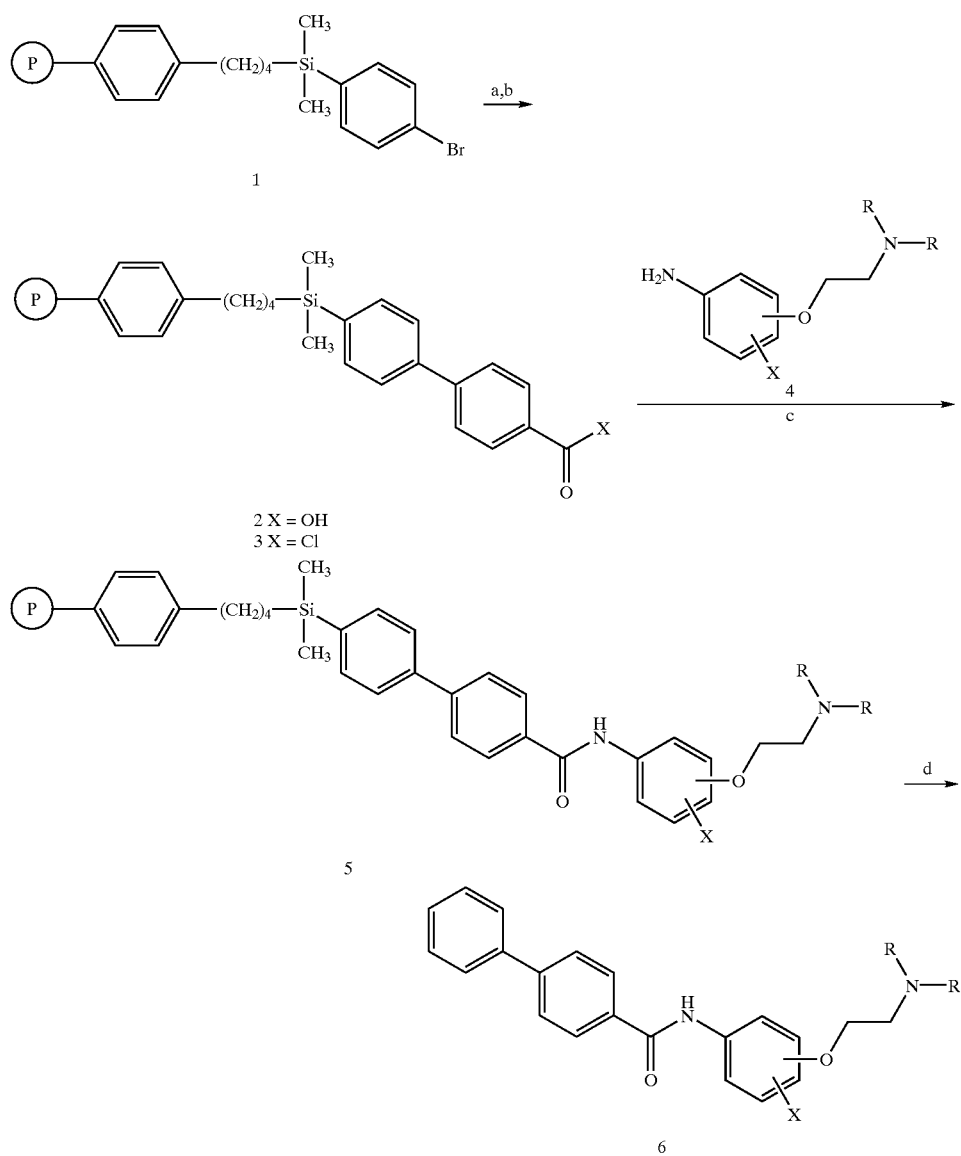

Scheme 1 a) caboxbezeneboronic acid, (Ph$_3$P)$_4$Pd, Na$_2$CO$_3$, EtOH, toluene, 90° C., 24 h; b) (COCl)$_2$, toluene; c) 4, diisopropylethylamine, CH$_2$Cl$_2$; d) CF$_3$CO$_2$H, CH$_2$Cl$_2$.

as N-bromosuccinimide and triphenylphosphine, in a suitable solvent, such as dichloromethane, dimethylformamide and pyridine, to afford 2-4. Treatment of 2-4 with a suitable acid and solvent, such as trifluoroacetic:dichloromethane:water (50:48:2) gives the desired benzanilide or biphenylcarboxanilide 2-5 which are compounds of formula (I).

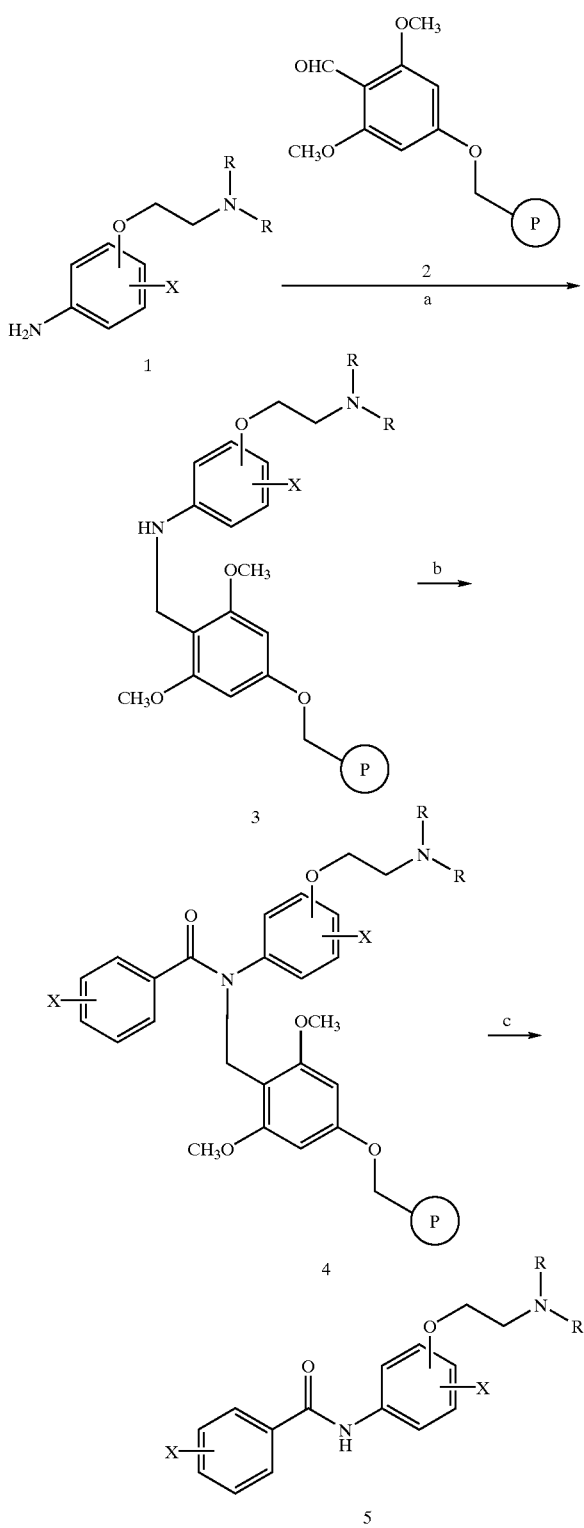

Scheme 2 a) BAL resin, NaBH(OAc)₃, 1% HOAc, DMF; b) X-benzoic acid, N-bromosuccinimide, Ph₃P, pyridine; c) TFA, CH₂Cl₂, H₂O.

The invention will now be described by reference to the following examples which are merely illustrative and are not to be construed as a limitation of the scope of the present invention. In the Examples, mass spectra were performed upon a VG Zab mass spectrometer using fast atom bombardment, unless otherwise indicated.

EXAMPLES

Preparation 1

Preparation of 4-(2-Diisopropylamino)ethoxy-3-methoxyaniline a) 4-(2-diisopropylamino)ethoxy-3-methoxy-1-nitrobenzene A mixture of 4-nitroguaiacole (1.0 g, 5.9 mmol), 2-diisopropylaminoethyl chloride hydrochloride (1.2 g, 5.9 mmol), and powdered potassium carbonate (1.38 g, 10 mmol) in dry acetone (100 mL) was heated to reflux, stirred for 16 h, cooled, filtered, and the filtrate was concentrated in vacuo. The residue was partitioned between ethyl acetate (300 mL) and water (40 mL), and the organic phase was washed with water (40 mL), dried (Na₂SO₄), and concentrated in vacuo to give the title compound: MS(ES) m/e 297.2 [M+H]⁺.

b) 4-(2-diisopropylamino)ethoxy-3-methoxyaniline

A mixture of the compound of Preparation 1(a) (1.6 g, 5.4 mmol) and 5% palladium-on-carbon (0.3 g) in absolute ethanol (100 mL) was shaken in a hydrogen atmosphere (50 psi) for 2.5 h, filtered, and the filtrate was concentrated in vacuo to give the title compound: MS(ES) m/e 267.3 [M+H]⁺.

Preparations 2–8

Preparation of 2-(2-Diisoprolylamino)ethoxy-4-methoxyaniline, 3-(2-Diisopropylamino)ethoxyaniline, 4-(2-Diisopropylamino)ethoxy-2-fluoroaniline, 4-(2-Diisopropylamino)ethoxyaniline, 2-(2-Diisopropylamino)ethoxyaniline, 3-(2-Diisopropylamino)ethoxy-2-methylaniline, and 3-(2-Diisopropylamino)ethoxy-4-methylaniline Following the procedure of Preparation 1, except substituting 5-methoxy-2-nitrophenol, 3-nitrophenol, 3-fluoro-4-nitrophenol, 4-nitrophenol, 2-nitrophenol, 2-methyl-3-nitrophenol, or 2-methyl-5-nitrophenol for 4-nitroguaiacole, gave the title compounds:

2-(2-diisopropylamino)ethoxy-4-methoxyaniline: MS(ES) m/e 267.2 [M+H]⁺;
3-(2-diisopropylamino)ethoxyaniline: MS(ES) m/e 237.2 [M+H]⁺;
4-(2-diisopropylamino)ethoxy-2-fluoroaniline: MS(ES) m/e 255.0 [M+H]⁺;
4-(2-diisopropylamino)ethoxyaniline: MS(ES) m/e 237.2 [M+H]⁺;
2-(2-diisopropylamino)ethoxyaniline: MS(ES) m/e 237.1 [M+H]⁺;
3-(2-diisopropylamino)ethoxy-2-methylaniline: MS(ES) m/e 251.2 [M+H]⁺; and
3-(2-diisopropylamino)ethoxy-4-methylaniline: MS(ES) m/e 251.1 [M+H]⁺.

Preparation 9

Preparation of 3-(2-Dicyclohexylamino)ethoxy-4-methoxyaniline a) N,N-dicyclohexyl-2-methoxy-5-nitro-phenoxyacetamide A solution of 2-methoxy-5-nitro-phenoxyacetyl chloride (0.22 g, 0.9 mmol), prepared from 2-methoxy-5-nitrophenoxyacetic acid (Brown et al., *J. Chem. Soc.* 1955, 3681) and thionyl chloride, in dichloromethane (10 mL) was added to a mixture of dicyclohexylamine (0.16 g, 0.9 mmol) and diisopropylethylamine (0.23 g, 1.76 mmol) in dichloromethane (20 mL), maintained at RT for 16 h, washed with water (2×20 mL), dried ($Na_2SO_4$), and concentrated in vacuo. The residue was recrystallized from methanol to afford the title compound (0.16 g).

b) N,N-dicyclohexyl-2-methoxy-5-amino-phenoxyacetamide

Following the procedure of Preparation 1(b), except substituting the compound of Preparation 9(a) for the compound of Preparation 1(a), gave the title compound.

c) 3-(2-dicyclohexylamino)ethoxy-4-methoxyaniline

A solution of the compound of Preparation 9(b)(0.15 g, 0.04 mmol) in anhydrous tetrahydrofuran (25 mL) was treated with 1.0M borane in tetrahydrofuran (4.3 mL, 4.3 mmol), heated to reflux for 3 h, maintained at RT for 16 h, carefully treated with methanol (5 mL), heated to reflux for 30 min, cooled, and concentrated in vacuo. The residue was partitioned between ethyl acetate (75 mL) and water (15 mL), and the organic phase was washed with water (15 mL), dried ($Na_2SO_4$), concentrated in vacuo, and the residue was purified by preparative TLC (Whatman PLK5F, 10% ethanol/dichloromethane-1% triethylamine) to give the title compound.

Preparation 10

Preparation 3-(2-Dipropylamino)ethoxy-4-methoxyaniline a) 3-(2-dipropylamino)ethoxy-4-methoxy-1-nitrobenzene A solution of 3-(2-bromoethoxy)-4-methoxy-1-nitrobenzene (Mutai et al., *Tetrahedron*, 1984, 40, 1755) (0.5 g, 1.8 mmol) and dipropylamine (1.8 g, 18 mmol) in dimethylformamide (10 mL) containing potassium iodide (0.28 g, 1.9 mmol) and potassium carbonate (0.42 g, 3 mmol) was warmed to 100° C. and stirred for 16 h. The mixture was cooled, diluted with dichloromethane (100 mL), filtered, and the filtrate was concentrated in vacuo. The residue was partitioned between ethyl acetate (150 mL) and water (30 mL), and the organic phase was washed with water (4×30 mL), dried ($Na_2SO_4$), and concentrated in vacuo to give the title compound: MS(ES) m/e 297.1 [M+H]$^+$.

b) 3-(2-dipropylamino)ethoxy-4-methoxyaniline

Following the procedure of Preparation 1(b), except substituting the compound of Preparation 10(a) for the compound of Preparation 1(a), gave the title compound: MS(ES) m/e 267.0 [M+H]$^+$.

Preparations 11–16

Preparation of 3-[2-(N-Cyclohexyl-N-isopropylamino)ethoxy]-4-methoxyaniline, 3-[2-(cis-2,6-Dimethylpiperidin-1-yl)ethoxy]-4-methoxyaniline, 3-[2-(N-Ethyl-N-isopropylamino)ethoxy]-4-methoxyaniline, 3-[2-(2,5-Dimethypyrrolidin-1-yl)ethoxy]-4-methoxyaniline, 4-Methoxy-3-[2-(2,2,6,6-tetramethylpiperidin-1-yl)ethoxy]aniline, and 3-[2-(N-t-Butyl-N-isopropyl)aminoethoxy]-4-methoxyaniline Following the procedure of Preparation 10, except substituting N-isopropylcyclohexylamine, cis-2,6-dimethylpiperidine, N-ethylisopropylamine, 2,5-dimethylpyrrolidine, 2,2,6,6-tetramethypiperidine, or N-tert-butylisopropylamine for dipropylamine, gave the title compounds:

3-[2-(N-cyclohexyl-N-isopropylamino)ethoxy]-4-methoxyaniline: MS(ES) m/e 307.2 [M+H]$^+$;

3-[2-(cis-2,6-dimethylpiperidin-1-yl)ethoxy]-4-methoxyaniline: MS(ES) m/e 279.3 [M+H]$^+$;

3-[2-(N-ethyl-N-isopropylamino)ethoxy]-4-methoxyaniline: MS(ES) m/e253.1 [M+H]$^+$;

3-[2-(2,5-dimethypyrrolidin-1-yl)ethoxy]-4-methoxyaniline: MS(ES) m/e 265.1 [M+H]$^+$;

4-methoxy-3-[2-(2,2,6,6-tetramethylpiperidin-1-yl)ethoxy]aniline: MS(ES) m/e 307.0 [M+H]$^+$; and 3-[2-(N-t-butyl-N-isopropyl)aminoethoxy]-4-methoxyaniline: MS(ES) m/e 281 [M+H]$^+$.

Preparations 17–18

Preparation of 3-[2-(N-Isopropyl-N-methylamino)ethoxy]-4-methoxyaniline and N-Ethyl-3-[2-(N-isopropyl-N-methylamino)ethoxy]-4-methoxyaniline a) 3-[2-(N-isopropyl-N-methylamino)ethoxy]-4-methoxy-1-nitrobenzene Following the procedure of Preparation 10(a), except substituting N-methylisopropylamine for dipropylamine, gave the title compound: MS(ES) m/e 269.4 [M+H]$^+$.

b) 3-[2-(N-isopropyl-N-methylamino)ethoxy]-4-methoxyaniline and N-ethyl-3-[2-(N-isopropyl-N-methylamino)ethoxy]-4-methoxyaniline Following the procedure of Preparation 1(b), except substituting the compound of Preparation 17(a) for the compound of Preparation 1(a), gave a mixture of the title compounds:

3-[2-(N-isopropyl-N-methylamino)ethoxy]-4-methoxyaniline: MS(ES) m/e 239.1 [M+H]$^+$; and N-ethyl-3-[2-(N-isopropyl-N-methylamino)ethoxy]-4-methoxyaniline: MS(ES) m/e 267.1 [M+H]$^+$.

Preparation 19

Preparation of 3-(3-Diisopropylamino)propyloxy-4-methoxyaniline a) 3-(3-bromopropoxy)-4-methoxy-1-nitrobenzene A stirred mixture of 2-methoxy-5-nitrophenol (5.0 g. 29.6 mmol) and powdered potassium carbonate (6.5 g, 47.4 mmol) in dimethylformamide (50 mL) was treated with 1,3-dibromopropane (80.8 g, 0.4 mol), heated to 90° C. for 2 h, cooled, diluted with dichloromethane (250 mL), and filtered. The filtrate was concentrated in vacuo and the residue was crystallized from methanol. The resulting solid was triturated with 30% ethyl acetate/hexane and then with boiling 30% ethyl acetate/hexane. The combined organic phases were concentrated in vacuo to give the title compound: $^1$H NMR (300 MHz, $CDCl_3$) δ7.92 (dd, 1H), 7.75 (d, 1H), 6.92 (dd, 1H), 4.20 (t, 2H), 3.95 (s, 3H), 3.62 (t, 2H), 2.40 (m, 2H).

b) 3-(3-diisopropylamino)propyloxy-4-methoxyaniline

Following the procedure of Preparation 1(b), except substituting the compound of Preparation 19(a) for the compound of Preparation 1(a), gave the title compound: MS(ES) m/e 281.1 [M+H]⁺.

Preparation 20

Preparation of 3-(3-Diisopropylamino)propyl-4-methoxyaniline a) N,N-diisopropyl-3-(2-methoxy-5-nitrophenyl) propionamide A solution of 3-(2-methoxy-5-nitrophenyl)propionyl chloride(0.46 g, 1.9 mmol), prepared from 3-(2-methoxy-5-nitrophenyl)propionic acid (Asano et al., *J. Pharm. Soc. Japan*, 1950, 70, 480) and thionyl chloride, in dichloromethane (5 mL) was added in one portion to a solution of diisopropylamine (0.67 g, 6.6 mmol) in dichloromethane (20 mL), stirred for 16 h, washed with water (2×20 mL), dried (Na₂SO₄), and concentrated in vacuo to give the title compound: MS(ES) m/3 309.1 [M+H]⁺.

b) N,N-diisopropyl-3-(2-methoxy-5-nitrophenyl) propylamine

A solution of the compound of Preparation 20(a)(0.6 g, 1.95 mmol) in dry tetrahydrofuran (50 mL) was treated with 1.0M borane in tetrahydrofuran (15 mL, 15 mmol), heated to reflux for 2 h, allowed to cool, stirred for 16 h, and carefully treated with methanol (10 mL). The mixture was concentrated in vacuo, and the residue was dissolved in dichloromethane (250 mL) and washed with water (2×40 mL). The organic phase was dried (Na₂SO₄) and concentrated in vacuo to give the title compound (0.52 g): MS(ES) m/3 295.1 [M+H]⁺.

c) 3-(3-diisopropylamino)propyl-4-methoxyaniline

Following the procedure of Preparation 1(b), except substituting the compound of Preparation 20(b) for the compound of Preparation 1(a), gave the title compound: MS(ES) m/e 265.3 [M+H]⁺.

Preparation 21

Preparation of 3-(2-Diisopropylamino)ethoxy-4-iodoaniline a) 3-(2-diisopropylamino)ethoxy-4-iodo-1-nitrobenzene Following the procedure of Preparation 1(a), except substituting 2-iodo-5-nitrophenol (Cambie et al., *Australian J. Chem.*, 1997, 50, 767) for 4-nitroguaiacole, gave the title compound: MS(ES) m/e 392.5 [M+H]⁺.

b) 3-(2-diisopropylamino)ethoxy-4-iodoaniline

A mixture of the compound of Preparation 21(a)(0.5 g, 1.27 mmol) and ferrous sulfate heptahydrate (10.0 g, 36 mmol) in water (50 mL) was stirred, heated to 100° C., and treated with concentrated ammonium hydroxide (6 mL) added dropwise over 5 min. The mixture was stirred for 5 min, cooled, filtered, and the filtrate was extracted with ethyl acetate. The organic phase was dried, concentrated in vacuo, and the residue was chromatographed (silica gel, 5% methanol/dichloromethane) to afford the title compound as a yellow solid (0.37 g): MS(ES) m/e 362.8 [M+H]⁺.

Preparation 22

Preparation of 3-(2-Diisopropylamino)ethoxy-4-ethylaniline Hydrochloride a) 3-(2-diisopropylamino)ethoxy-4-(trimethylsilylethynyl)-1-nitrobenzene A mixture of the compound of Preparation 21(a)(2.0 g, 5 mmol), trimethylsilylacetylene (0.8 g, 8 mmol), palladium acetate (15 mg), and triphenylphosphine (30 mg) in degassed triethylamine (25 mL) was heated to 90° C. for 16 h. The mixture was concentrated in vacuo and the residue was partitioned between ethyl acetate and water. The organic phase was washed with brine, dried, and concentrated in vacuo. The residue was purified by flash chromatography (silica gel, step gradient, 0–1% methanol/dichloromethane-ammonia) to afford the title compound (1.0 g): MS(ES) m/e 363 [M+H]⁺.

b) 3-(2-diisopropylamino)ethoxy-4-ethynyl-1-nitrobenzene

A solution of the compound of Preparation 22(a)(1 g, 2.7 mmol) in methanol (20 mL) was treated with potassium carbonate (100 mg), stirred for 5 h, concentrated in vacuo, and the residue was dissolved in dichloromethane, and washed with 5% aqueous sodium carbonate and with brine. The organic phase was dried (MgSO₄) and concentrated in vacuo to afford the title compound (0.75 g): MS(ES) m/e 291.1 [M+H]⁺.

c) 3-(2-diisopropylamino)ethoxy-4-ethylaniline hydrochloride

A mixture of the compound of Preparation 22(b)(0.73 g, 2.5 mmol) (0.6 g) and 10% palladium-on-carbon (200 mg) in 1:1 methanol/ethanol (60 mL) was shaken in a hydrogen atmosphere for 4 h, filtered through Supercel, and the filtrate was concentrated in vacuo. The residue was dissolved in ethyl acetate, treated with ethereal hydrogen chloride, stirred, and filtered to give the title compound (0.6 g): MS(ES) m/e 265.1 [M+H]⁺.

Preparation 23

Preparation of 3-(2-Diisopropylamino)ethoxy-4-(methoxycarbonylamino)aniline a) 3-(2-diisopropylamino)ethoxy-4-nitroaniline hydrochloride Following the procedure of Preparation 1(a), except substituting 2-amino-5-nitrophenol for 4-nitroguaiacole, gave the title compound: MS(ES) m/e 281.9 [M+H]⁺.

b) 3-(2-diisopropylamino)ethoxy-4-(methoxycarbonylamino)-1-nitrobenzene

A solution of the compound of Preparation 23(a) (1.27 g, 4 mmol) and diisopropylethylamine (2.1 mL, 12 mmol) in dichloromethane (25 mL) was treated with methyl chloroformate (0.38 g, 4 mmol), stirred for 7 d, treated with water, and the organic phase was washed with brine, dried, and concentrated in vacuo. The residue was purified by flash chromatography (silica gel, step gradient, 0–1% methanol/dichloromethane-ammonia) to afford the title compound: MS (ES) m/e 339.9 [M+H]⁺.

c) 3-(2-diisopropylamino)ethoxy-4-(methoxycarbonylamino)aniline

Following the procedure of Preparation 1(b), except substituting the compound of Preparation 23(b) for the compound of Preparation 1(a), gave the title compound: MS(ES) m/e 310.0 [M+H]⁺.

Preparation 24

Preparation of 3-(2-Diisopropylamino)ethoxy-4-methoxy-N-methyl-aniline a) N-formyl-3-(2-diisopropylamino)ethoxy-4-methoxyaniline A mixture of formic acid (0.3 g, 6.4 mmol) and acetic anhydride (0.53 g, 5.2 mmol) was heated to 50° C. for 2 h, cooled, diluted with anhydrous tetrahydrofuran (10 mL), and treated in one portion with a solution of 3-(2-diisopropylamino)ethoxy-4-methoxyaniline (WO 95/15954) (0.5 g, 2 mmol) in tetrahydrofuran (5 mL). The resulting mixture was stirred for 16 h, concentrated in vacuo, and the residue was partitioned between ethyl acetate (85 mL) and 5% aqueous sodium carbonate (10 mL). The organic phase was washed with 5% sodium carbonate (10 mL) and then with brine (10 mL), dried ($Na_2SO_4$), and concentrated in vacuo to afford the title compound (0.57 g): MS(ES) m/e 295.4 $[M+H]^+$.

b) 3-(2-diisopropylamino)ethoxy-4-methoxy-N-methyl-aniline

A solution of the compound of Preparation 24(a)(0.57 g, 1.9 mmol) in dry tetrahydrofuran (25 mL) was treated with 2.0M borane in tetrahydrofuran (2.4 mL, 4.8 mmol), stirred, and heated to reflux for 3 h. The mixture was cooled, maintained at RT for 18 h, carefully treated with methanol (10 mL), heated to reflux for 1 h, cooled, and concentrated in vacuo. The residue was partitioned between ethyl acetate (25 mL) and water (25 mL), and the organic phase was washed with water (25 mL) and with brine (25 mL), dried ($Na_2SO_4$), and concentrated in vacuo to afford the title compound (0.5 g): MS(ES) m/e 281.4 $[M+H]^+$.

Preparations 25–26

Preparation of 2-Dimethylaminomethyl-1,4-benzodioxan-6-amine and 2-Dimethylaminomethyl-1,4-benzodioxan-7-amine a) 2-chloromethyl-6-nitro-1,4-benzodioxan and 2-chloromethyl-7-nitro-1,4-benzodioxan Following the procedure of *Gazz. Chim. Ital.*, 87, 1038–49 (1958), 2-chloromethyl-1,4-benzodioxan (2 g, 11 mmol) in glacial acetic acid (15 mL) was stirred, cooled, and treated with nitric acid (11 mL) added over 5 min. The mixture was heated to 95° C. for 40 min, cooled, and carefully poured into water. The resulting mixture was extracted with chloroform, and the organic layer was washed and dried ($Na_2SO_4$). The residue was distilled, bp 166–8° C./1 mm Hg, to give a mixture of the title compounds (1.39 g).

b) 2-dimethylaminomethyl-6-nitro-1,4-benzodioxan and 2-dimethylaminomethyl-7-nitro-1,4-benzodioxan The compounds of Preparation 25(a)–26(a)(1.64 g, 7 mmol) were dissolved in excess dimethylamine (15 mL) and heated to 150° C. in a pressure vessel for 16 h. The mixture was cooled, triturated with ether, and filtered. The filtrate was concentrated in vacuo and the residue was distilled, bp 120–30° C./1 mm Hg, to give the title compounds (788 mg) as an orange oil. The product was purified further by acid/base treatment to give a mixture of the title compounds (600 mg).

c) 2-dimethylaminomethyl-1,4-benzodioxan-6-amine and 2-dimethylaminomethyl-1,4-benzodioxan-7-amine The compounds of Preparation 25(b)–26(b)(600 mg, 2.5 mmol) and 10% palladium-on-carbon (200 mg) in ethanol (30 mL) were stirred under hydrogen (1 atm) for 1 h. The mixture was filtered, concentrated in vacuo, and chromatographed (silica gel, step gradient, 0–4% methanol/chloroform) followed by thick layer chromatography (step gradient, 1–2% methanol/chloroform) to give the title compounds:

2-dimethylaminomethyl-1,4-benzodioxan-6-amine, TLC $R_f$ 0.56 (silica gel, 10% ethanol/chloroform); and
2-dimethylaminomethyl-1,4-benzodioxan-7-amine, TLC $R_f$ 0.51 (silica gel, 10% ethanol/chloroform).

Example 1

Preparation of N-[3-(2-Diisopropylamino)ethoxy-4-methoxyphenyl]-[1,1'-biphenyl]-4-carboxamide A solution of 4-biphenylcarbonyl chloride (0.32 g, 1.5 mmol), prepared from 4-biphenylcarboxylic acid and thionyl chloride, was added in one portion to a solution 3-(2-diisopropylamino)ethoxy-4-methoxyaniline (WO 95/15954)(0.37 g, 1.5 mmol) and diisopropylethylamine (0.19 g, 1.5 mmol) in dichloromethane (20 mL). The resulting mixture was stirred for 16 h, extracted with 5% aqueous sodium carbonate (10 mL), dried ($Na_2SO_4$), and concentrated in vacuo. The residue was purified by flash chromatography (silica gel, 10% methanol/dichloromethane) to give the title compound (0.22 g): MS(ES) m/e 447.1 $[M+H]^+$.

Example 2

Preparation of N-[3-(2-Diisopropylamino)ethoxy-4-methoxyphenyl]-2'-methyl-1,1'-biphenyl]-4-carboxamide Following the procedure of Example 1, except substituting 2'-methyl-4-biphenylcarboxylic acid (Klein et al., *J. Med. Chem.* 1998, 41, 437) for 4-biphenylcarboxylic acid, gave the title compound: MS(ES) m/e 461.3 $[M+H]^+$.

Example 3

Preparation of N-[3-(2-Diisopropylamino)ethoxy-4-methoxyphenyl]-[1,1'-biphenyl]-3-carboxamide Following the procedure of Example 1, except substituting 3-biphenylcarboxylic acid for 4-biphenylcarboxylic acid, gave the title compound: MS(ES) m/e 447.3 $[M+H]^+$.

Examples 4–11

Preparation of N-[3-(2-Dimethylamino)ethoxy-phenyl]-[1,1'-biphenyl]-4-carboxamide; N-[4-(2-Dimethylamino)ethoxy-phenyl]-[1,1'-biphenyl]-4-carboxamide; N-[2-(3-Dimethylamino)propoxy-phenyl]-[1,1'-biphenyl]-4-carboxamide; N-[3-(3-Dimethylamino)propoxy-phenyl]-[1,1'-biphenyl]-4-carboxamide; N-[4-(3-Dimethylamino)propoxy-phenyl]-[1,1'-biphenyl]-4-carboxamide; N-[3-(Diethylamino)ethoxy-4-methoxyphenyl]-[1,1'-biphenyl]-4-carboxamide; N-[3-[2-(Piperidin-1-yl)ethoxy]-4-methoxyphenyl]-[1,1'-biphenyl]-4-carboxamide; and N-[3-[2-(4-Morpholinyl)ethoxy]-4-methoxyphenyl]-[1,1'-biphenyl]-4-carboxamide Following the procedure of Example 1, except substituting 3-(2-dimethylamino)ethoxyaniline (WO 95/26328), 4-(2-dimethylamino)ethoxyaniline (WO 96/23769), 2-(3-dimethylamino)-propoxyaniline (WO/9515954), 3-(3-dimethylamino)propoxyaniline (WO95/15954), 4-(3-dimethylamino)propoxyaniline (U.S. Pat. No. 3,994,900), 3-(2-diethylamino)ethoxy-4-methoxyaniline (WO 95/15954), 3-[2-(piperidin-1-yl)ethoxy]-4-methoxyaniline (WO 95/15954), or 3-[2-(4-morpholinyl)ethoxy]-4-methoxyaniline (WO 95/15954) for 3-(2-diisopropylamino)ethoxy-4-methoxyaniline, gave the title compounds:

N-[3-(2-dimethylamino)ethoxy-phenyl]-[1,1'-biphenyl]-4-carboxamide: MS(ES) m/e 361 [M+H]$^+$;
N-[4-(2-dimethylamino)ethoxy-phenyl]-[1,1'-biphenyl]-4-carboxamide: MS(ES) m/e 361 [M+H]$^+$;
N-[2-(3-dimethylamino)propoxy-phenyl]-[1,1'-biphenyl]-4-carboxamide: MS(ES) m/e 375 [M+H]$^+$;
N-[3-(3-dimethylamino)propoxy-phenyl]-[1,1'-biphenyl]-4-carboxamide: MS(ES) m/e 373 [M–H]$^+$;
N-[4-(3-dimethylamino)propoxy-phenyl]-[1,1'-biphenyl]-4-carboxamide: MS(ES) m/e 375 [M+H]$^+$;
N-[3-(diethylamino)ethoxy-4-methoxyphenyl]-[1,1'-biphenyl]-4-carboxamide: MS(ES) m/e 419.5 [M+H]$^+$;
N-[3-[2-(piperidin-1-yl)ethoxy]-4-methoxyphenyl]-[1,1'-biphenyl]-4-carboxamide: MS(ES) m/e 431.3 [M+H]$^+$; and
N-[3-[2-(4-morpholinyl)ethoxy]-4-methoxyphenyl]-[1,1'-biphenyl]-4-carboxamide: MS(ES) m/e 433.0 [M+H]$^+$.

Examples 12–13

Preparation of N-[3-(2-Diisopropylamino)ethoxy-2-methylphenyl]-2'-methyl-4'-(5-methyl-1,2,4-oxadiazol-3-yl)-[1,1'-biphenyl]-4-carboxamide and N-[3-(2-Diisopropylamino)ethoxy-phenyl]-2'-methyl-4'-(5-methyl-1,2,4-oxadiazol-3-yl)-[1,1'-biphenyl]-4-carboxamide Following the procedure of Example 1, except substituting the compounds of Preparation 7 or Preparation 3 for 3-(2-diisopropylamino)ethoxy-4-methoxyaniline and substituting 2'-methyl-4'-(5-methyl-1,2,4-oxadiazol-3-yl) biphenyl]-4-carboxylic acid (EP 0533268) for 4-biphenylcarboxylic acid, gave the title compounds:

N-[3-(2-diisopropylamino)ethoxy-2-methylphenyl]-2'-methyl-4'-(5-methyl-1,2,4-oxadiazol-3-yl)-[1,1'-biphenyl]-4-carboxamide: MS(ES) m/e 527.3 [M+H]$^+$; and
N-[3-(2-diisopropylamino)ethoxy-phenyl]-2'-methyl-4'-(5-methyl-1,2,4-oxadiazol-3-yl)-[1,1'-biphenyl]-4-carboxamide: MS(ES) m/e 513.2 [M+H]$^+$.

Example 14

Preparation of N-[3-(2-Dipropylamino)ethoxy-4-methoxyphenyl]-[1,1'-biphenyl]-4-carboxamide Following the procedure of Example 1, except substituting the compound of Preparation 10(b) for 3-(2-diisopropylamino)ethoxy-4-methoxyaniline, gave the title compound MS(ES) m/e 447.1 [M+H]$^+$.

Examples 15–22

Preparation of N-[3-(2-Dicyclohexylamino)ethoxy-4-methoxyphenyl]-[1,1'-biphenyl]-4-carboxamide; N-[3-[2-(N-Cyclohexyl-N-isopropylamino)ethoxy]-4-methoxyphenyl]-[1,1'-biphenyl]-carboxamide; N-[3-[2-(cis-2,6-Dimethylpiperidin-1-yl)ethoxy]-4-methoxylphenyl]-[1,1'-biphenyl]-4-carboxamide; N-[3-[2-(N-Ethyl-N-isopropylamino)ethoxy]-4-methoxyphenyl]-[1,1'-biphenyl]-4-carboxamide; N-[3-[2-(2,5-Dimethypyrrolidin-1-yl)ethoxy]-4-methoxyphenyl]-[1,1'-biphenyl]-4-carboxamide; N-[4-Methoxy-3-[2-(2,2,6,6-tetramethylpiperidin-1-yl)ethoxy]phenyl]-1,1'-biphenyl-4-carboxamide; N-[3-[2-(N-tert-Butyl-N-isopropyl)aminoethoxy]-4-methoxyphenyl]-[1,1'-biphenyl]-4-carboxamide; and N-[3-(2-Diisopropylamino)ethoxy-4-methylphenyl]-[1,1'-biphenyl]-4-carboxamide Following the procedure of Example 1, except substituting the compounds of Preparation 9, Preparations 11–16, or Preparation 8, for 3-(2-diisopropylamino)ethoxy-4-methoxyaniline, gave the title compounds:

N-[3-(2-dicyclohexylamino)ethoxy-4-methoxyphenyl]-[1,1'-biphenyl]-4-carboxamide: MS(ES) m/e 527.5 [M+H]$^+$;
N-[3-[2-(N-cyclohexyl-N-isopropylamino)ethoxy]-4-methoxyphenyl]-[1,1'-biphenyl]-carboxamide: MS(ES) m/e 487.2 [M+H]$^+$;
N-[3-[2-(cis-2,6-dimethylpiperidin-1-yl)ethoxy]-4-methoxyphenyl]-[1,1'-biphenyl]-4-carboxamide: MS(ES) m/e 459.0 [M+H]$^+$;
N-[3-[2-(N-ethyl-N-isopropylamino)ethoxy]-4-methoxyphenyl]-[1,1'-biphenyl]-4-carboxamide: MS(ES) m/e 433.1 [M+H]$^+$;
N-[3-[2-(2,5-dimethypyrrolidin-1-yl)ethoxy]-4-methoxyphenyl]-[1,1'-biphenyl]-4-carboxamide: MS(ES) m/e 445.0 [M+H]$^+$;
N-[4-methoxy-3-[2-(2,2,6,6-tetramethylpiperidin-1-yl)ethoxy]phenyl]-1,1'-biphenyl-4-carboxamide: MS(ES) m/e 486.9 [M+H]$^+$;
N-[3-[2-(N-tert-butyl-N-isopropyl)aminoethoxy]-4-methoxyphenyl]-[1,1'-biphenyl]-4-carboxamide: MS(ES) m/e 460.9 [M+H]$^+$; and
N-[3-(2-diisopropylamino)ethoxy-4-methylphenyl]-[1,1'-biphenyl]-4-carboxamide: MS(ES) m/e 431.0 [M+H]$^+$.

Example 23

Preparation of N-[3-(3-Diisopropylamino)propyloxy-4-methoxyphenyl]-[1,1'-biphenyl]-4-carboxamide Following the procedure of Example 1, except substituting the compound of Preparation 19(b) for 3-(2-diisopropylamino)ethoxy-4-methoxyaniline, gave the title compound: MS(ES) m/e 461.0 [M+H]$^+$.

Example 24

Preparation of N-[3-(3-Diisopropylamino)propyl-4-methoxyphenyl]-[1,1'-biphenyl]-4-carboxamide Following the procedure of Example 1, except substituting the compound of Preparation 20(c) for 3-(2-diisopropylamino)ethoxy-4-methoxyaniline, gave the title compound: MS(ES) m/e 445.2 [M+H]$^+$.

Example 25

Preparation of N-[3-(2-Diisopropylamino)ethoxy-4-iodophenyl]-[1,1'-biphenyl]-4)-4-carboxamide Following the procedure of Example 1, except substituting the compound of Preparation 21(b) for 3-(2-diisopropylamino)ethoxy-4-methoxyaniline, gave the title compound: MS(ES) m/e 542.9 [M+H]$^+$.

Example 26

Preparation of N-[3-(2-Diisopropylamino)ethoxy-4-ethylphenyl]-[1,1'-biphenyl]-4-carboxamide Following the procedure of Example 1, except substituting the compound of Preparation 22(c) for 3-(2-diisopropylamino)ethoxy-4-methoxyaniline, gave the title compound: MS(ES) m/e 445.1 [M+H]$^+$.

Example 27

Preparation of N-[3-(2-Diisopropylamino)ethoxy-4-(methoxycarbonylamino)phenyl]-[1,1'-biphenyl]-4-carboxamide Following the procedure of Example 1, except substituting the compound of Preparation 23(c) for 3-(2- diisopropylamino)ethoxy-4-methoxyaniline, gave the title compound: MS(ES) m/e 490.1 [M+H]+.

Example 28

Preparation of N-[1,1'-Biphenyl]-4-yl-3-(2-diisopropylamino)ethoxy-4-methoxybenzamide a) N-[1,1'-biphenyl]-4-yl-3-hydroxy-4-methoxybenzamide

A solution of 3-hydroxy-4-methoxybenzoic acid (0.5 g, 3 mmol) in dichloromethane and dimethylformamide was cooled to −20° C., and N-bromosuccinimide (0.57 g, 3.2 mmol) and triphenylphosphine (0.8 g, 3.1 mmol) were added in one portion. The mixture was stirred at −20° C. for 10 min, and treated with a solution of 4-aminobiphenyl (0.5 g, 3 mmol) and dry pyridine (0.3 g, 3.8 mmol) in dichloromethane (5 mL). The mixture was allowed to warm to RT, stirred 20 h, concentrated in vacuo, and the residue was stirred in 5% methanol/dichloromethane (40 mL) and filtered. The filtrate was concentrated in vacuo, chromatographed (silica gel, 5% methanol/dichloromethane), and fractions containing the product were pooled, concentrated in vacuo, and dissolved in dichloromethane from which the title compound precipitated (0.11 g): MS(ES) m/e 320 [M+H]+.

b) N-[1,1'-biphenyl]-4-yl-3-(2-diisopropylamino)ethoxy-4-methoxybenzamide

Following the procedure of Preparation 1(a), except substituting the compound of Example 28(a) for 4-nitroguaiacole, gave the title compound: MS(ES) m/e 446.6 [M+H]+.

Example 29

Preparation of N-[3-(2-Diisopropylamino)ethoxy-4-methoxyphenyl]-[1,1'-biphenyl]-4-methanamine Dihydrochloride A solution of the compound of Example 1 (70 mg, 0.16 mmol) in anhydrous tetrahydrofuran (25 mL) was treated with 1.0M borane in tetrahydrofuran (1.56 mL, 1.56 mmol), heated to reflux for 3 h, cooled, maintained at RT for 16 h, carefully treated with methanol (5 mL), stirred for 1 h, and concentrated in vacuo. The residue was partitioned between ethyl acetate (50 mL) and water (10 mL), and the organic phase was dried (Na$_2$SO$_4$), concentrated in vacuo, dissolved in dichloromethane, and treated with ethereal hydrogen chloride to afford the title compound (51 mg): MS(ES) m/e 433.3 [M+H]+.

Examples 30–31

Preparation of N-[3-(2-Diisopropylamino)ethoxy-4-methoxy-phenyl]-4'-cyano-1,1'-biphenyl-4-carboxamide and N-[3-(2-Diisopropylamino)ethoxy-4-methoxyphenyl]-4'-cyano-2'-methyl-1,1'-biphenyl-4-carboxamide Following the procedure of Example 1, except substituting 4'-cyano-4-biphenylcarboxylic acid (WO 94/12181) or 4'-cyano-4'-methyl-4-biphenylcarboxylic acid (WO 96/19477) for 4-biphenylcarboxylic acid, gave the title compounds:

N-[3-(2-diisopropylamino)ethoxy-4-methoxy-phenyl]-4'-cyano-1,1'-biphenyl-4-carboxamide): MS(ES) m/e 472.0 [M+H]+; and N-[3-(2-diisopropylamino)ethoxy-4-methoxyphenyl]-4'-cyano-2'-methyl-1,1'-biphenyl-4-carboxamide): MS(ES) m/e 486.0 [M+H]+.

Example 32

Preparation of N-[3-(2-Diisopropylamino)ethoxy-4-(ethoxycarbonyl)phenyl]-[1,1'-biphenyl]-4-carboxamide Following the procedure of Example 1, except substituting 3-(2-diisopropylamino)ethoxy-4-(ethoxycarbonyl) aniline (Clinton, et al., *J. Am. Chem. Soc.* 1957, 79, 2290) for 3-(2-diisopropylamino)ethoxy-4-methoxyaniline, gave the title compound: MS(ES) m/e 489.1 [M+H]+.

Example 33

Preparation of N-[3-(2-Diisopropylamino)ethoxy-4-methoxyphenyl]-2-naphthalenecarboxamide Following the procedure of Example 1, except substituting 2-naphthalenecarboxylic acid for 4-biphenylcarboxylic acid, gave the title compound: MS(ES) m/e 421.3 [M+H]+.

Example 34

Preparation of N-(1'-Methylspiro[benzofuran-3(2H), 4'-piperidin]-5-yl-[1,1'-biphenyl]-4-carboxamide Following the procedure of Example 1, except substituting 1'-methyl-spiro[benzofuran-3(2H),4'-piperidin]-5-amine (WO 96/11934) for 3-(2-diisopropylamino)ethoxy-4-methoxyaniline, gave the title compound: MS(ES) m/e 399.2 [M+H]+.

Examples 35–36

Preparation of N-[3-[2-(N-Isopropyl-N-methylamino)ethoxy]-4-methoxyphenyl]-[1,1'-biphenyl]-4-carboxamide and N-Ethyl-N-[3-[2-(N-isopropyl-N-methylamino)ethoxy]-4-methoxyphenyl]-1,1'-biphenyl-4-carboxamide Following the procedure of Example 1, except substituting the compounds of Preparations 17(b) and 18(b) for 3-(2-diisopropylamino)ethoxy-4-methoxyaniline gave the title compounds:

N-[3-[2-(N-isopropyl-N-methylamino)ethoxy]-4-methoxyphenyl]-[1,1'-biphenyl]-4-carboxamide: MS(ES) m/e 419.1 [M+H]+; and N-ethyl-N-[3-[2-(N-isopropyl-N-methylamino)ethoxy]-4-methoxyphenyl]-1,1'-biphenyl-4-carboxamide: MS (ES) m/e 446.3 [M+H]+.

Example 37

Preparation of N-Methyl-N-[3-(2-diisopropylamino) ethoxy-4-methoxyphenyl]-2'-methyl-4'-(5-methyl-1,2,4-oxadiazol-3-yl)-[1,1'-biphenyl]-4-carboxamide Following the procedure of Example 1, except substituting the compound of Preparation 24(b) for 3-(2-diisopropylamino)ethoxy-4-methoxyaniline and substituting 2'-methyl-4'-(5-methyl-1,2,4-oxadiazol-3-yl)biphenyl]-4-carboxylic acid (EP 0533268) for 4-biphenylcarboxylic acid, gave the title compound: MS(ES) m/e 557.3 [M+H]+.

Example 38

Preparation of N-Methyl-N-[3-(diisopropylamino) ethoxy-4-methoxyphenyl]-[1,1'-biphenyl]-4-carboxamide Following the procedure of Example 1, except substituting the compound of Preparation 24(b) for 3-(2- diisopropylamino)ethoxy-4-methoxyaniline, gave the title compound: MS(ES) m/e 461.3 [M+H]+.

Example 39

Preparation of N-[4-(2-Diisopropylamino)ethoxy-3-methoxyphenyl]-[1,1'-biphenyl]-4-carboxamide a) resin-bound 4'-(4-biphenylcarboxylic acid)

Resin-bound phenylbromide (WO 98/17695, 3-Scheme18)(1.0 g, 1.22 mmol) was swelled in a mixture of toluene (10 mL) and ethanol (4 mL) for 30 min, and treated with 4-carboxybenzeneboronic acid (0.6 g, 3.6 mmol), tetrakis(triphenylphosphine)palladium(0) (0.2 g), and 2M aqueous sodium carbonate (3.6 mL, 7.2 mmol). The mixture heated to reflux for 24 h, cooled, and the resin was filtered and washed sequentially with dichloromethane, methanol, 1:1 methanol/water containing 15 drops of concentrated hydrochloric acid, 1:1 methanol/water, dichloromethane, and methanol. The resulting resin was dried in vacuo.

b) resin-bound 4'-(biphenyl-4-carbonyl chloride)

The resin of Example 39(a) (0.06 g) and oxalyl chloride (0.13 g, 1 mmol) in toluene (10 mL) was shaken for 16 h, filtered, and washed with toluene and dichloromethane.

c) resin bound 4'-[N-[4-(2-diisopropylamino)ethoxy-3-methoxyphenyl]-[1,1'-biphenyl]-4-carboxamide]

A mixture of the resin of Example 39(b), the compound of Preparation 1(b)(0.13 g, 0.5 mmol), and diisopropylethylamine (0.05 g, 0.4 mmol) in dichloromethane (15 mL) was shaken for 20 h, the resin was filtered, washed with dichloromethane (3×20 mL) and with methanol (2×20 mL), and dried in vacuo for 16 h.

d) N-[4-(2-diisopropylamino)ethoxy-3-methoxyphenyl]-[1,1'-biphenyl]-4-carboxamide A mixture of the resin of Example 39(c), trifluoroacetic acid (3 mL) and dichloromethane (0.5 mL) was stirred for 20 h, and the resin was filtered and washed with methanol (3×10 mL). The filtrate was concentrated in vacuo, and the residue was partitioned between dichloromethane (50 mL) and 10% aqueous sodium hydroxide (5 mL). The organic phase was washed with water, dried ($Na_2SO_4$), and concentrated in vacuo to give the title compound: MS(ES) m/e 447.4 [M+H]+.

Examples 40–44

Preparation of N-[2-(2-Diisopropylamino)ethoxy-4-methoxyphenyl]-[1,1'-biphenyl]-4-carboxamide; N-[3-(2-Diisopropylamino)ethoxy-phenyl]-[1,1'-biphenyl]-4-carboxamide; N-[2-Fluoro-4-(2-diisopropylamino)ethoxy-phenyl]-1,1'-biphenyl]-4-carboxamide; N-[4-(2-Diisopropylamino)ethoxyphenyl]-[1,1'-biphenyl]-4-carboxamide; and N-[2-(2-Diisopropylamino)ethoxy-phenyl]-[1,1'-biphenyl]-4-carboxamide Following the procedure of Example 39(c)–39(d), except substituting the compounds of Preparations 2–6 for the compound of Preparation 1, gave the title compounds:

N-[2-(2-diisopropylamino)ethoxy-4-methoxyphenyl]-[1,1'-biphenyl]-4-carboxamide: MS(ES) m/e 447.3 [M+H]+;
N-[3-(2-diisopropylamino)ethoxy-phenyl]-[1,1'-biphenyl]-4-carboxamide: MS(ES) m/e 417.5 [M+H]+;
N-[2-fluoro-4-(2-diisopropylamino)ethoxy-phenyl]-[1,1'-biphenyl]-4-carboxamide: MS(ES) m/e 435.4 [M+H]+;
N-[4-(2-diisopropylamino)ethoxy-phenyl]-[1,1'-biphenyl]-4-carboxamide MS(ES) m/e 417.4 [M+H]+; and
N-[2-(2-diisopropylamino)ethoxy-phenyl]-[1,1'-biphenyl]-4-carboxamide: MS(ES) m/e 417.4 [M+H]+.

Example 45

Preparation of N-[3-(2-Diisopropylamino)ethoxy-4-methoxyphenyl]-4-(iodo)benzamide a) [3-(2-diisopropylamino)ethoxy-4-methoxyaniline/(4-formyl-3,5-dimethoxyphenoxy)-Merrifield resin adduct A mixture of 4-formyl-3,5-dimethoxyphenoxy-Merrifield resin (Boojamra et al., *J. Org. Chem.* 1995, 60, 5742), 3-(2-diisopropylamino)ethoxy-4-methoxyaniline (WO 9515954), and sodium triacetoxyborohydride in dimethyformamide containing 1% acetic acid was shaken to afford the title adduct.

b) N-[3-(2-diisopropylamino)ethoxy-4-methoxyphenyl]-4-iodobenzamide/(4-formyl-3,5-dimethoxyphenoxy)-Merrifield resin adduct The resin of Example 45(a) in dimethylformamide was treated with pyridine and with an excess of a mixture of equivalent amounts of 4-iodobenzoic acid, N-bromosuccinimide and triphenylphosphine. The resin was washed to afford the title adduct.

c) N-[3-(2-diisopropylamino)ethoxy-4-methoxyphenyl]-4-iodobenzamide

The resin of Example 45(b) was stirred in a mixture of trifluoroacetic acid:dichloromethane:water (50:48:2), filtered, and the filtrate concentrated in vacuo to afford the title compound: MS(ES) m/e 497.8 [M+H]+.

Examples 46–70

Following the procedure of Example 45, except using 3-(2-diethylamino)ethoxy-aniline (WO 95/15954), 4-(2-diethylamino)ethoxy-aniline (Wyatt et al., *J. Med. Chem.,* 1995, 38, 1657), 3-(2-diethylamino)ethoxy-4-methoxyaniline (WO 96/23769), 3-(2-diisopropylamino)ethoxy-4-methoxyaniline (WO 95/15954), and the compounds of Preparation 3 and Preparation 5, and using 4-isopropylbenzoic acid, 4-cyclohexylbenzoic acid, 4'-ethyl-4-biphenylcarboxylic, 4-nitrobenzoic acid, 4-methoxybenzoic acid, 3-bromobenzoic acid, 3-iodobenzoic acid, 4-bromobenzoic acid, and 4-iodobenzoic acid gave the following compounds:

N-[3-(2-diisopropylamino)ethoxy-4-methoxyphenyl]-4-iodobenzamide: MS(ES) m/e 497.0 [M+H]+;
N-[3-(2-diisopropylamino)ethoxy-4-methoxyphenyl]-4-bromobenzamide: MS(ES) m/e 449.0 [M+H]+;
N-[3-(2-diisopropylamino)ethoxy-4-methoxyphenyl]-3-bromobenzamide: MS(ES) m/e 449.0 [M+H]+;
N-[3-(2-diisopropylamino)ethoxy-4-methoxyphenyl]-4-(isopropyl)benzamide: MS(ES) m/e 413.2 [M+H]+;
N-[3-(2-diisopropylamino)ethoxy-4-methoxyphenyl]-4'-ethyl-[1,1'-biphenyl]-4-carboxamide: MS(ES) m/e 475.2 [M+H]+;
N-[3-(2-diisopropylamino)ethoxy-4-methoxyphenyl]-4-(methoxy)benzamide: MS(ES) m/e 401.3 [[M+H]+;

N-[3-(2-diisopropylamino)ethoxy-4-methoxyphenyl]-4-(nitro)benzamide: MS(ES) m/e 416.5 [M+H]+;
N-[4-(2-diisopropylamino)ethoxy-phenyl]-4-iodobenzamide: MS(ES) m/e 467.0 [M+H]+;
N-[3-(2-diisopropylamino)ethoxy-4-methoxyphenyl]-3-iodobenzamide: MS(ES) m/e 497.0 [M+H]+;
N-[3-(2-diethylamino)ethoxy-4-methoxyphenyl]-3-iodobenzamide: MS(ES) m/e 460.0 [M+H]+;
N-[4-(2-diisopropylamino)ethoxy-phenyl]-3-iodobenzamide: MS(ES) m/e 467.0 [M+H]+;
N-[3-(2-diisopropylamino)ethoxy-phenyl]-3-iodobenzamide: MS(ES) m/e 476.0 [M+H]+;
N-[3-(2-diethylamino)ethoxy-phenyl]-3-iodobenzamide: MS(ES) m/e 439.0 [M+H]+;
N-[3-(2-diethylamino)ethoxy-4-methoxyphenyl]-4-bromobenzamide: MS(ES) m/e 423.0 [M+H]+;
N-[4-(2-diisopropylamino)ethoxy-phenyl]-4-bromobenzamide: MS(ES) m/e 418.8 [M+H]+;
N-[3-(2-diethylamino)ethoxy-4-methoxyphenyl]-3-bromobenzamide: MS(ES) m/e 423.0 [M+H]+;
N-[4-(2-diisopropylamino)ethoxy-phenyl]-3-bromobenzamide: MS(ES) m/e 418.8 [M+H]+;
N-[4-(2-diisopropylamino)ethoxy-phenyl]-4-(isopropyl)benzamide: MS(ES) m/e 383.2 [M+H]+;
N-[3-(2-diethylamino)ethoxy-4-methoxyphenyl]-4-(cyclohexyl)benzamide: MS(ES) m/e 425.2 [M+H]+;
N-[4-(2-diisopropylamino)ethoxy-phenyl]-4-(cyclohexyl)benzamide: MS(ES) m/e 423.0 [M+H]+;
N-[4-(2-diethylamino)ethoxy-phenyl]-4-(cyclohexyl)benzamide: MS(ES) m/e 395.0 [M+H]+;
N-[3-(2-diethylamino)ethoxy-4-methoxyphenyl]-4'-ethyl-[1,1'-biphenyl]-4-carboxamide: MS(ES) m/e 447.2 [M+H]+;
N-[4-(2-diisopropylamino)ethoxy-phenyl]-4'-ethyl-[1,1'-biphenyl]-4-carboxamide: MS(ES) m/e 445.2 [M+H]+;
N-[4-(2-diethylamino)ethoxy-phenyl]-4'-ethyl-[1,1'-biphenyl]-4-carboxamide: MS(ES) m/e 417.4 [M+H]+; and
N-[3-(2-diisopropylamino)ethoxy-phenyl]-4'-ethyl-[1,1'-biphenyl]-4-carboxamide: MS(ES) m/e 445.2 [M+H]+.

Examples 71–73

Preparation of N-[3-(2-Diisopropylamino)ethoxy-4-methoxyphenyl]-3,4-dichlorobenzamide, N-[3-(2-Diisopropylamino)ethoxy-4-methoxyphenyl]-3,5-dichlororbenzamide, and N-[3-(2-Diisopropylamino)ethoxy-4-methoxy-phenyl]-4-(cyclohexyl)benzamide Following the procedure of Example 1, except substituting 3,4-dichlorobenzoic acid, 3,5-dichlorobenzoic acid or 4-cyclohexylbenzoic acid for 4-biphenylcarboxylic acid, gave the title compounds:

N-[3-(2-diisopropylamino)ethoxy-4-methoxyphenyl]-3,4-dichlorobenzamide: MS(ES) m/e 439.3 [M+H]+;
N-[3-(2-diisopropylamino)ethoxy-4-methoxyphenyl]-3,5-dichlororbenzamide: MS(ES) m/e 439.2 [M+H]+; and
N-[3-(2-diisopropylamino)ethoxy-4-methoxy-phenyl]-4-(cyclohexyl)benzamide: MS(ES) m/e 453.0 [M+H]+.

Example 74

Preparation of N-[3-(2-Diisopropylamino)ethoxy-4-methoxyphenyl]-3-methoxy-[1,1'-biphenyl]-4-carboxamide a) N-[3-(2-diisopropylamino)ethoxy-4-methoxyphenyl]-4-(4,4,5,5-tetramethyl-1,3,2-dioxaborolan-2-yl)benzamide/(4-formyl-3,5-dimethoxyphenoxy)-Merrifield resin adduct Following the procedure of Example 45(b), except substituting 4-(4,4,5,5-tetramethyl-1,3,2-dioxaborolan-2-yl) benzoic acid (Guiles et al., *J. Org. Chem.* 1996, 61, 5169) for 4-iodobenzoic acid, gave the title adduct.

b) N-[3-(2-diisopropylamino)ethoxy-4-methoxyphenyl]-3'-methoxy-[1,1'-biphenyl]-4-carboxamide/(4-formyl-3,5-dimethoxyphenoxy)-Merrifield resin adduct Following the general procedure of Guiles et al., *J. Org. Chem.* 1996, 61, 5169, the adduct of Example 74(a) in dimethylformamide was reacted with 3-iodoanisole, tetrakis(triphenylphosphine)palladium(0), and aqueous potassium carbonate at 80° C. for 18 h to afford the title adduct.

c) N-[3-(2-diisopropylamino)ethoxy-4-methoxyphenyl]-3'-methoxy-[1,1'-biphenyl]-4-carboxamide Following the procedure of Example 45(c), except substituting the adduct of Example 74(b) for the adduct of Example 42(b), gave the title compound: MS(ES) m/e 477.2 [M+H]+.

Examples 75–81

Preparation of N-[3-(2-Dimethylamino)ethoxy-4-methoxyphenyl]-4'-methoxy-[1,1'-biphenyl]-4-carboxamide; N-[3-(2-Dimethylamino)ethoxy-4-methoxyphenyl]-4'-hydroxy-[1,1-biphenyl]-4-carboxamide; N-[3-(2-Diisopropylamino)ethoxy-4-methoxyphenyl]-4'-acetyl-[1,1'-biphenyl]-4-carboxamide N-[3-(2-Diethylamino)ethoxy-4-methoxyphenyl]-3'-methoxy-[1,1'-biphenyl]-4-carboxamide N-[3-(2-Dimethylamino)ethoxy-4-methoxyphenyl]-3'-methoxy-[1,1'-biphenyl]-4-carboxamide N-[3-(2-Diisopropylamino)ethoxy-4-methoxyphenyl]-3'-hydroxy-[1,1'-biphenyl]-4-carboxamide and N-[3-(2-Dimethylamino)ethoxy-4-methoxyphenyl]-3'-hydroxy-[1,1'-biphenyl]-4-carboxamide Following the procedure of Example 74, except using 3-(2-diisopropylamino)ethoxy-4-methoxyaniline (WO 95/15954), 3-(2-diethylamino)ethoxy-4-methoxyaniline, and 3-(2-dimethylamino)ethoxy-4-methoxyaniline, and using 3-iodophenol, 3-iodoanisole, and 4'-iodoacetophenone, gave the title compounds:

N-[3-(2-dimethylamino)ethoxy-4-methoxyphenyl]-4'-methoxy-[1,1'-biphenyl]-4-carboxamide MS(ES) m/e 421.0 [M+H]+;
N-[3-(2-dimethylamino)ethoxy-4-methoxyphenyl]-4'-hydroxy-[1,1'-biphenyl]-4-carboxamide MS(ES) m/e 407.2 [M+H]+;
N-[3-(2-diisopropylamino)ethoxy-4-methoxyphenyl]-4'-acetyl-[1,1'-biphenyl]-4-carboxamide: MS(ES) m/e 489.2 [M+H]+;
N-[3-(2-diethylamino)ethoxy-4-methoxyphenyl]-3'-methoxy-[1,1'-biphenyl]-4-carboxamide: MS(ES) m/e 449.2 [M+H]+;
N-[3-(2-dimethylamino)ethoxy-4-methoxyphenyl]-3'-methoxy-[1,1'-biphenyl]-4-carboxamide: MS(ES) m/e 421.0 [M+H]+;
N-[3-(2-diisopropylamino)ethoxy-4-methoxyphenyl]-3'-hydroxy-[1,1'-biphenyl]-4-carboxamide: MS(ES) m/e 463.2 [M+H]+; and
N-[3-(2-dimethylamino)ethoxy-4-methoxyphenyl]-3'-hydroxy-[1,1'-biphenyl]-4-carboxamide MS(ES) m/e 407.2 [M+H]+.

Example 82

Preparation of N-[2-(Dimethylaminomethyl)-1,4-benzodioxan-7-yl]-2'-methyl-4'-(5-methyl-1,2,4-oxadiazol-3-yl)biphenyl-4-carboxamide The compound of Preparation 26(c)(188 mg, 0.6 mmol) in tetrahydrofuran (30 mL) was treated with a solution of sodium hydroxide (55 mg) in water (1 mL) and 2'-methyl-4'-(5-methyl-1,2,4-oxadiazol-3-yl)-biphenyl-4-carbonyl chloride (WO 95/15954)(0.6 mmol) was added. The mixture was stirred for 16 h, concentrated in vacuo, and partitioned between water and chloroform. The organic phase was dried ($Na_2SO_4$) and concentrated in vacuo to give a white foam which was chromatographed (basic alumina, ethyl acetate) to give the title compound. mp 92–94° C.

Example 84

Preparation of N-[2-(dimethylaminomethyl)-1,4-benzodioxan-6-yl]-2'-methyl-4'-(5-methyl-1,2,4-oxadiazol-3-yl)biphenyl-4-

Following the procedure of Example 82, except substituting the compound of Preparation 25(c) for the compound of Preparation 26(c), gave the title compound. mp 188–190° C.

Biological Data

CCR5 Receptor Binding Assay

CHO cell membranes ($0.25 \times 10^6$ cell equivalents) derived from CHO cells stably transfected with CCR5 were incubated with $0.3^{125}$I-RANTES in a 96 well plate for 45 min. at room temperature (final reaction volume 200 ul). The reaction was terminated by filtration and the filters (GF/C) were washed twelve times with a solution of phosphate buffered saline containing 0.1% bovine serum albumin and 0.05% $NaN_3$. The radioactivity bound to filters was measured by liquid scintillation spectrometry. Non-specific binding was determined in the presence of unlabelled RANTES (10 or 30 nM) and averages 30–50% of total binding.

CCR5 Receptor Functional Assay

The cellular functional assay used to assess antagonist activity of compounds was RANTES-induced $Ca^{2+}$ mobilization in RBL 2H3 cells stably expressing the hCCR5 receptor (RBL 2H3 hCCR5). Agonist activity is determined by $Ca^{2+}$ mobilization in the same cells which is inhibitable by a selective CCR5 antagonist. Cells were grown to 80–100% confluency in T-150 flasks and washed with phosphate-buffered saline. Cells were lifted from the flasks by treating with 3 mL of 1 mM EDTA for 3 min. at room temperature and diluting to $2 \times 10^6$ cells/mL with Krebs Ringer Henseleit buffer (KRH; 118 mM NaCl, 4.6 mM KCl, 25 mM $NaHCO_3$, 1 mM $KH_2PO_4$ and 11 mM glucose) containing 5 mM HEPES (pH 7.4), 1 mM $CaCl_2$, 1 mM $MgCl_2$ and 0.1% BSA and centrifuged at 200 g for 3 min. Cells were resuspended at $2 \times 10^6$ cells/mL in the same buffer with 2 μM Fura-2AM, and incubated for 35 min. at 370° C. Cells were centrifuged at 200×g for 3 min. and resuspended in the same buffer without Fura-2AM, then incubated for 15 min. at 37° C. to complete the hydrolysis of intracellular Fura-2AM, and then centrifuged as before. Cells ($10^6$ cells/mL) were resuspended in cold KRH with 5 mM HEPES (pH 7.4), 1 mM $CaCl_2$, 1 mM $MgCl_2$ and 0.1% gelatin and maintained on ice until assayed. For antagonist studies, aliquots (2 mL) of cells were prewarmed at 37° C. for 5 min. in 3 mL plastic cuvettes and fluorescence measured in a fluorometer (Johnson Foundation Biomedical Group, Philadelphia, Pa., USA) with magnetic stirring and temperature maintained at 37° C. Excitation was set at 340 nm and emission set at 510 nm. Various concentrations of antagonists or vehicle were added and fluorescence monitored for ~15 sec to ensure that there was no change in baseline fluorescence, followed by the addition of 33 nM RANTES. Maximal $Ca^{2+}$ attained after 33 nM RANTES stimulation was calculated as described by Grynkiewicz et al., (1985). The percent of maximal RANTES-induced $Ca^{2+}$ was determined for each concentration of antagonist and the $IC_{50}$, defined as the concentration of test compound that inhibits 50% of the maximal 33 nM RANTES response, obtained from the concentration-response curves (5–7 concentrations of antagonists).

The compounds of this invention show CCR5 receptor ligand activity having $IC_{50}$ values in the range of 0.0001 to 100 μM. The full structure/activity relationship has not yet been established for the compounds of this invention. However, given the disclosure herein, one of ordinary skill in the art can utilize the present assays in order to determine which compounds of formula (I) are ligands of the CCR5 receptor and which bind thereto with an $IC_{50}$ value in the range of 0.0001 to 100 μM.

All publications, including, but not limited to, patents and patent applications cited in this specification, are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration it is believed that one skilled in the art can, given the preceding description, utilize the present invention to its fullest extent. Therefore any examples are to be construed as merely illustrative and not a limitation on the scope of the present invention in any way. The embodiments of the invention in which an exclusive property or privilege is claimed are defined as follows.

What is claimed is:

1. A method of treating a CCR5-mediated disease state in mammals which comprises administering to a mammal in need of such treatment, an effective amount of a compound of formula (I) or a pharmaceutically acceptable salt thereof:

Ar—A—E    Formula I in which Ar represents a group selected from (i), (ii) or (iii);

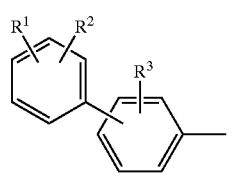

(i)

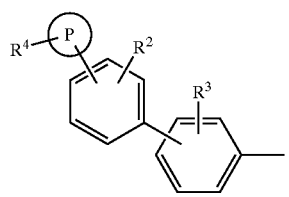

(ii)

-continued

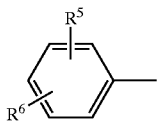
(iii)

in which:
R$^1$ and R$^2$ are independently hydrogen, C$_{1-6}$alkyl, C$_{2-6}$alkenyl, C$_{2-6}$alkynyl, C$_{3-7}$cycloalkyl, C$_{3-6}$cycloalkenyl, aryl, (CH$_2$)$_a$NR$^7$R$^8$, (CH$_2$)$_a$NR$^7$COR$^9$, (CH$_2$)$_a$NR$^7$CO$_2$R$^{10}$, (CH$_2$)$_a$NR$^7$SO$_2$R$^{11}$, (CH$_2$)$_a$CONR$^{12}$R$^{13}$, hydroxy C$_{1-6}$alkyl, C$_{1-4}$alkoxyalkyl (optionally substituted by a C$_{1-4}$alkoxy or hydroxy group), (CH$_2$)$_a$CO$_2$C$_{1-6}$alkyl, (CH$_2$)$_b$OC(O)R$^{14}$, CR$^{15}$=NOR$^{16}$, CNR$^{15}$=NOR$^{16}$, COR$^{17}$, CONR$^{12}$R$^{13}$, CONR$^{12}$(CH$_2$)$_c$OC$_{1-4}$alkyl, CONR$^{12}$(CH$_2$)$_a$CO$_2$R$^{18}$, CONHNR$^{19}$R$^{20}$, CONR$^{12}$SO$_2$R$^{21}$, CO$_2$R$^{22}$, cyano, trifluoromethyl, NR$^7$R$^8$, NR$^7$COR$^9$, NR$^{23}$CO(CH$_2$)$_a$NR$^{23}$R$^{24}$, NR$^{23}$CONR$^{23}$R$^{24}$, NR$^7$CO$_2$R$^{10}$, NR$^7$SO$_2$R$^{11}$, N=CNR$^{23}$NR$^{23}$R$^{24}$, nitro, hydroxy, C$_{1-6}$alkoxy, hydroxyC$_{1-6}$alkoxy, C$_{1-6}$alkoxyC$_{1-6}$alkoxy, OC(O)NR$^{25}$R$^{26}$, SR$^{27}$, SOR$^{28}$, SO$_2$R$^{28}$, SO$_2$NR$^{25}$R$^{26}$ or halogen;
a is 1, 2, 3 or 4;
R$^7$ and R$^8$ are independently hydrogen or C$_{1-6}$alkyl, or NR$^7$R$^8$ forms a heterocyclic ring which has 5 or 6 ring members which, may optionally be substituted by an oxo group and, when there are 6 ring members, may optionally contain in the ring one oxygen or sulfur atom;
R$^9$ is hydrogen, C$_{1-6}$alkyl or C$_{1-4}$alkoxyalkyl;
R$^{10}$ is C$_{1-6}$alkyl;
R$^{11}$ is C$_{1-6}$alkyl or phenyl;
R$^{12}$ and R$^{13}$ are independently hydrogen or C$_{1-6}$alkyl, or NR$^{12}$R$^{13}$ forms a saturated heterocyclic ring which has 5 or 6 members which, when there are 6 ring members, may optionally contain in the ring one oxygen or sulfur atom;
b is 0, 1, 2 or 3;
R$^{14}$ is C$_{1-4}$alkyl, optionally substituted by a C$_{1-6}$alkoxy;
R$^{15}$ and R$^{16}$ are independently hydrogen or C$_{1-6}$alkyl;
R$^{17}$ is hydrogen or C$_{1-6}$alkyl;
c is 1, 2 or 3;
R$^{18}$ is hydrogen or C$_{1-6}$alkyl;
R$^{19}$ and R$^{20}$ are independently hydrogen or C$_{1-6}$alkyl;
R$^{21}$ is hydrogen or C$_{1-6}$alkyl;
R$^{22}$ is hydrogen or C$_{1-6}$alkyl optionally substituted with one or two substituents selected from C$_{1-6}$alkyl, C$_{1-6}$alkoxy, hydroxy, or NR$^7$R$^8$;
R$^{23}$ and R$^{24}$ are independently hydrogen or C$_{1-6}$alkyl;
R$^{25}$ and R$^{26}$ are independently hydrogen or C$_{1-6}$alkyl, or NR$^{25}$R$^{26}$ forms a saturated heterocyclic ring which has 5 or 6 members, when there are 6 ring members, may optionally contain in the ring one oxygen or sulfur atom;
R$^{27}$ is hydrogen or C$_{1-6}$alkyl;
R$^{28}$ is C$_{1-6}$alkyl;
P is a 5 to 7-membered heterocyclic ring containing 1 to 4 heteroatoms selected from oxygen, nitrogen or sulfur;
R$^3$ and R$^4$ are independently hydrogen, C$_{1-6}$alkyl, C$_{3-7}$cycloalkyl, C$_{3-6}$cycloalkenyl, hydroxyC$_{1-6}$alkyl, C$_{1-6}$alkylOC$_{1-6}$alkyl, CONR$^{29}$R$^{30}$, CO$_2$R$^{31}$, cyano, aryl, trifluoromethyl, NR$^{29}$R$^{30}$, nitro, hydroxy, C$_{1-6}$alkoxy, acyloxy or halogen;

R$^{29}$, R$^{30}$ and R$^{31}$ are independently hydrogen or C$_{1-6}$alkyl;
R$^5$ is hydrogen, C$_{1-6}$alkyl, C$_{1-6}$alkoxy or halogen;
R$^6$ is hydrogen, C$_{1-6}$alkyl, C$_{3-7}$cycloalkyl (optionally substituted by a hydroxy or an oxo group), hydroxyC$_{1-6}$alkyl, hydroxyC$_{3-6}$alkenyl, hydroxyC$_{3-6}$alkynyl, (CH$_2$)$_d$OR$^{32}$, (CH$_2$)$_d$COR$^{33}$, (CH$_2$)$_d$CR$^{34}$=NOR$^{35}$, CONR$^{36}$R$^{37}$, CO$_2$R$^{38}$, hydroxy, O(CH$_2$)$_e$R$^{39}$, NR$^{36}$R$^{37}$, SR$^{40}$, SO$_2$NR$^{41}$R$^{42}$ or halogen;
d is 0, 1, 2, 3, 4, 5, or 6;
R$^{32}$ is C$_{1-6}$alkyl, hydroxyC$_{1-6}$alkyl, or C$_{1-4}$alkanoyl;
R$^{33}$ is hydrogen or C$_{1-6}$alkyl;
R$^{34}$ is hydrogen or C$_{1-6}$alkyl;
R$^{35}$ is hydrogen or C$_{1-6}$alkyl;
R$^{36}$ and R$^{37}$ are independently hydrogen or C$_{1-6}$alkyl or NR$^{36}$R$^{37}$ forms a saturated heterocyclic ring which has 5 or 6 members, may optionally be substituted by an oxo group and, when there are 6 ring members, may optionally contain one oxygen or sulfur atom or an NH or NR$^{43}$ where R$^{43}$ is C$_{1-6}$alkyl, COR$^{44}$ or CO$_2$R$^{45}$ where R$^{44}$ and R$^{45}$ are independently hydrogen or C$_{1-6}$alkyl;
R$^{38}$ is hydrogen or C$_{1-6}$alkyl;
e is 1, 2, 3, 4, 5 or 6;
R$^{39}$ is C$_{1-6}$alkoxy, CO$_2$H, CO$_2$C$_{1-6}$alkyl or CONR$^{36}$R$^{37}$;
R$^{40}$ is C$_{1-6}$alkyl;
R$^{41}$ and R$^{42}$ are independently hydrogen or C$_{1-6}$alkyl;
alternatively, R$^5$ and R$^6$ form a fused benzo ring optionally substituted with C$_{1-6}$ alkyl, C$_{1-6}$alkoxy or halogen;
when Ar is (i), (ii) or (iii), and A is CONR$^{46}$, [NHCO, —NHCH$_2$,] or CH$_2$NH, where R$^{46}$ is hydrogen or C$_{1-6}$alkyl, E represents (a):

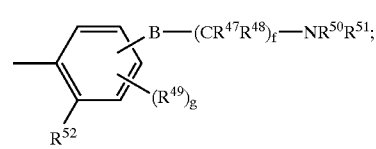
(a)

in which
R$^{47}$ and R$^{48}$ are independently hydrogen or C$_{1-6}$alkyl;
R$^{49}$ is hydrogen, C$_{1-6}$alkyl, CO$_2$R$^{53}$, NHCO$_2$R$^{54}$, hydroxy, C$_{1-6}$alkoxy or halogen where R$^{53}$ is hydrogen or C$_{1-6}$alkyl and R$^{54}$ is C$_{1-6}$alkyl;
R$^{50}$ and R$^{51}$ are independently hydrogen, C$_{1-6}$alkyl, C$_{3-7}$cycloalkyl, aralkyl, or together with the nitrogen atom to which they are attached form an optionally substituted 5- to 7-membered heterocyclic ring containing one to two heteroatoms selected from oxygen, nitrogen or sulfur;
B is oxygen, S(O)$_h$ where h is 0, 1 or 2, CR$^{55}$=CR$^{56}$ or CR$^{55}$R$^{56}$ where R$^{55}$ and R$^{56}$ are independently hydrogen or C$_{1-6}$alkyl, or B is NR57 where R$^{57}$ is hydrogen, C$_{1-6}$alkyl or phenylC$_{1-6}$alkyl;
R$^{52}$ is hydrogen or R$^{52}$ taken together with R$^{46}$ forms a group D where D is (CR$^{58}$R$^{59}$)$_i$ where i is 2, 3 or 4 and R$^{58}$ and R$^{59}$ are independently hydrogen or C$_{1-6}$alkyl or D is (CR$^{58}$R$^{59}$)$_j$—G where j is 0, 1, 2 or 3 and G is oxygen, sulfur or CR$^{58}$=CR$^{59}$;
f is 1 to 4; and
g is 1 or 2;
provided that the compound of formula (I) is not N-[3-(2-Dimethylaminoethoxy)-4-methoxyphenyl]-4'-(5-dimethylamino-1,2,4-oxadiazol-3-yl)-2'-methylbiphenyl-4- carboxamide; N-[3-(1-Methylazetidin-2-ylmethoxy)-4-methoxyphenyl]-4'-(5-methyl-1,2,4-oxadiazol-3-yl)-2'-methylbiphenyl-4-carboxamide; [7-(2-Dimethylaminoethoxy)-6-methoxy-3,4-dihydro-2H-quinolin-1-yl]-[2'-methyl-[1,2,4]-oxadiazol-3-yl)biphenyl-4-yl]-methanone oxalate; 2,3,6,7-Tetrahydro-1'-methyl-5-[2'-methyl-4'-(5-methyl-1,2,4-oxadiazol-3-yl)biphenyl-4-carbonyl]-furo[2,3-f]indole-3-spiro-3'-piperidine oxalate; 5-[4'-(5-Methyl-1,2,4-oxadiazol-3-yl)biphenyl-4-carbonyl]-1'-methyl-2,3,6,7-tetrahydrofuro[2,3-f]indole-3-spiro-4'-piperidine; 1'-Ethyl-5-[2'-methyl-4'-(5-methyl-1,2,4-oxadiazol-3-yl)-biphenyl-4-carbonyl]-2,3,6,7-tetrahydrospirofuro[2,3-f]indole-3,4'-piperidine; N-[2-(2-Dimethylamino)ethoxy-phenyl]-[1,1'-biphenyl]-4-carboxamide; N-[3-(2-Diisopropylamino)ethoxy-4-methoxyphenyl]benzamide; N-[3-(2-Diisopropylamino)ethoxy-4-methoxyphenyl]-[1,1'-biphenyl]-2-carboxamide; N-[3-(2-Diethylamino)ethoxy-4-methoxyphenyl]-4-(methoxy)benzamide; N-[3-(2-Diethylamino)ethoxy-4-methoxyphenyl]-4-(nitro)benzamide; N-[3-(2-Diethylamino)ethoxy-4-methoxyphenyl]-4-(nitro)benzamide; N-[3-(2-Dimethylamino)ethoxy-4-methoxyphenyl]-4-(nitro)benzamide; N-[3-(Dimethylamino)ethoxy-4-methoxyphenyl]-[1,1'-biphenyl]-4-carboxamide; N-[3-(2-Dimethylamino)ethoxy-4-methoxyphenyl]-4'-chloro-[1,1'-biphenyl]-4-carboxamide; N-[3-(2-Diethylamino)ethoxy-4-methoxyphenyl]-4'-hydroxy-[1,1'-biphenyl]-4-carboxamide; N-[3-(2-Diethylamino)ethoxy-4-methoxyphenyl]-4'-acetyl-[1,1'-biphenyl]-4-carboxamide; N-[3-(2-Dimethylamino)ethoxy-4-methoxyphenyl]-4'-acetyl-[1,1'-biphenyl]-4-carboxamide; N-[3-(2-Dimethylamino)ethoxy-4-methoxyphenyl]-3'-chloro-[1,1'-biphenyl]-4-carboxamide; N-[3-(2-Diethylamino)ethoxy-4-methoxyphenyl]-3'-nitro-[1,1'-biphenyl]-4-carboxamide; N-[3-(2-Dimethylamino)ethoxy-4-methoxyphenyl]-3'-nitro-[1,1'-biphenyl]-4-carboxamide; N-[3-(2-Diethylamino)ethoxy-4-methoxyphenyl]-4-iodobenzamide; N-[4-(2-Diethylamino)ethoxy-phenyl]-4-iodobenzamide; N-[2-(2-Diisopropylamino)ethoxy-phenyl]-4-iodobenzamide; N-[4-(2-Diethylamino)ethoxy-phenyl]-3-iodobenzamide; N-[2-(2-Diisopropylamino)ethoxy-phenyl]-3-iodobenzamide; N-[2-(2-Diethylamino)ethoxy-phenyl]-3-iodobenzamide; N-[3-(2-Diethylamino)ethoxy-phenyl]-4-bromobenzamide; N-[2-(2-Diisopropylamino)ethoxy-phenyl]-4-bromobenzamide; N-[2-(2-Diethylamino)ethoxy-phenyl]-4-bromobenzamide; N-[4-(2-Diethylamino)ethoxy-phenyl]-3-bromobenzamide; N-[2-(2-Diisopropylamino)ethoxy-phenyl]-3-bromobenzamide; N-[2-(2-Diethylamino)ethoxy-phenyl]-3-bromobenzamide; N-[3-(2-Diethylamino)ethoxy-4-methoxyphenyl]-4-(dimethylamino)benzamide; N-[4-(2-Diisopropylamino)ethoxy-phenyl]-4-(dimethylamino)benzamide; N-[4-(2-Diethylamino)ethoxy-phenyl]-4-(dimethylamino)benzamide; N-[2-(2-Diisopropylamino)ethoxy-phenyl]-4-(dimethylamino)benzamide; N-[2-(2-Diethylamino)ethoxy-phenyl]-4-(dimethylamino)benzamide; N-[4-(2-Diethylamino)ethoxy-phenyl]-4-(isopropyl)benzamide; N-[2-(2-Diisopropylamino)ethoxy-phenyl]-4-(isopropyl)benzamide; N-[2-(2-Diethylamino)ethoxy-phenyl]-4-(isopropyl)benzamide; N-[3-(2-Diethylamino)ethoxy-phenyl]-4-(cyclohexyl)benzamide; N-[2-(2-Diisopropylamino)ethoxy-phenyl]-4-(cyclohexyl)benzamide; N-[2-(2-Diethylamino)ethoxy-phenyl]-4-(cyclohexyl)benzamide; N-[2-(2-Diisopropylamino)ethoxy-phenyl]-4'-ethyl-[1,1'-biphenyl]-4-carboxamide; and N-[2-(2-Diethylamino)ethoxy-phenyl]-4'-ethyl-[1,1'-biphenyl]-4-carboxamide.

2. The method as claimed in claim 1 wherein the compound of formula (I) is a compound selected from:

N-[3-(3-Dimethylamino)propoxy-4-methoxyphenyl]-2'-methyl-4'-(5-methyl-1,2,4-oxadiazol-3-yl)-(1,1'-biphenyl)-4-carboxamide;

N-[3-(2-Piperidine)ethoxy-4-methoxyphenyl]-2'-methyl-4'-(5-methyl-1,2,4-oxadiazol-3-yl)-(1,1'-biphenyl)-4-carboxamide;

N-[3-(3-Dimethylaminopropyl)-4-methoxyphenyl]-2'-methyl-4'-(5-methyl-1,2,4-oxadiazol-3-yl)biphenyl-4-carboxamide oxalate;

N-[3-(1-Methyl-4-piperidyl)-4-methoxyphenyl]-2'-methyl-4'-(5-methyl-1,2,4-oxadiazol-3-yl)biphenyl-4-carboxamide oxalate;

N-[3-(1-Methyl-3-piperidyl)methoxyphenyl]-2'-methyl-4'-(5-methyl-1,2,4-oxadiazol-3-yl)biphenyl-4-carboxamide oxalate;

[3-(Dimethylaminoethyl)-3,6,7,8-tetrahydro-2H-furo[2,3-g]quinolin-5-yl]-[2'-methyl-4'-(5-methyl-[1,2,4]-oxadiazol-3-yl)-biphenyl-4-yl]-methanone oxalate;

5-[4-(2-Methyl-4-(5-methyl-1,2,4-oxadiazol-3-yl)phenyl)benzoylamino]-spiro[(2,3-dihydrobenzofuran)-3,4'-(1-methylhexahydroazepine)]oxalate;

2,3,5,6,7,8,-Hexahydro-1'-methyl-5-{2'-methyl-4'-[(5-methyl-1,2,4-oxadiazol-3-yl)biphenyl-4-yl]carbonyl}furo[2,3-g]quinoline-3-spiro-4'-piperidine oxalate;

6,7,8,9-Tetrahydro-1'-methyl-5-[[2'-methyl-4'-(5-methyl-1,2,4-oxadiazol-3-yl)[1,1'-biphenyl]-4-yl]carbonyl]-spiro[2H-furo[2,3-h][1]benzazepine-3(5H),4'-piperidine];

2,3,5,6,7,8-Hexahydro-5-[4'-(5-hydroxymethyl-1,2,4-oxadiazol-3-yl)-2'-methylbiphenyl-4-carbonyl]-1'-methylspiro[furo[2,3-g]quinoline-3,4'-piperidine] hydrochloride;

4'-(Dimethylamino)-5-[2'-methyl-4'-[(5-methyl-1,2,4-oxadiazol-3-yl)-biphenyl-4-yl]carbonyl]-2,3,6,7-tetrahydrospiro[furo[2,3-f]indole-3,1'-cyclohexane] hydrochloride;

N-[3-(2-Diisopropylamino)ethoxy-4-methoxyphenyl]-[1,1'-biphenyl]-3-carboxamide;

N-[3-(3-Dimethylamino)propoxy-phenyl]-[1,1'-biphenyl]-4-carboxamide;

N-[4-(3-Dimethylamino)propoxy-phenyl]-[1,1'-biphenyl]-4-carboxamide;

N-[3-(Diethylamino)ethoxy-4-methoxyphenyl]-[1,1'-biphenyl]-4-carboxamide;

N-[3-[2-(Piperidin-1-yl)ethoxy]-4-methoxyphenyl]-[1,1'-biphenyl]-4-carboxamide;

N-[3-(2-Diisopropylamino)ethoxy-2-methylphenyl]-2'-methyl-4'-(5-methyl-1,2,4-oxadiazol-3-yl)-[1,1'-biphenyl]-4-carboxamide;

N-[3-(2-Dipropylamino)ethoxy-4-methoxyphenyl]-[1,1'-biphenyl]-4-carboxamide;

N-[3-(2-Diisopropylamino)ethoxy-4-methylphenyl]-[1,1'-biphenyl]-4-carboxamide

N-[3-(2-Diisopropylamino)ethoxy-4-ethylphenyl]-[1,1'-biphenyl]-4-carboxamide;

N-[3-(2-Diisopropylamino)ethoxy-4-(methoxycarbonylamino)phenyl]-[1,1'-biphenyl]-4-carboxamide;

N-[1,1'-Biphenyl]-4-yl-3-(2-diisopropylamino)ethoxy-4-methoxybenzamide;

N-[3-(2-Diisopropylamino)ethoxy-4-(ethoxycarbonyl)phenyl]-[1,1'-biphenyl]-4-carboxamide;

N-[4-(2-Diisopropylamino)ethoxy-3-methoxyphenyl]-[1,1'-biphenyl]-4-carboxamide;

N-[2-(2-Diisopropylamino)ethoxy-4-methoxyphenyl]-[1,1'-biphenyl]-4-carboxamide;
N-[3-(2-diisopropylamino)ethoxy-phenyl]-[1,1'-biphenyl]-4-carboxamide;
N-[2-Fluoro-4-(2-diisopropylamino)ethoxy-phenyl]-[1,1'-biphenyl]-4-carboxamide;
N-[4-(2-Diisopropylamino)ethoxy-phenyl]-[1,1'-biphenyl]-4-carboxamide;
N-[2-(2-Diisopropylamino)ethoxy-phenyl]-[1,1'-biphenyl]-4-carboxamide;
N-[3-(2-Diisopropylamino)ethoxy-4-methoxyphenyl]-4-bromobenzamide;
N-[3-(2-Diisopropylamino)ethoxy-4-methoxyphenyl]-4-(isopropyl)benzamide;
N-[3-(2-Diisopropylamino)ethoxy-4-methoxyphenyl]-4-(cyclohexyl)benzamide;
N-[3-(2-Diisopropylainino)ethoxy-4-methoxyphenyl]-3,4-dichlorobenzamide;
N-[3-(2-Diisopropylamino)ethoxy-4-methoxyphenyl]-3,5-dichlororbenzamide;
N-[3-(2-Diisopropylamino)ethoxy-4-methoxyphenyl]-4-(nitro)benzamide;
N-[3-(2-Diisopropylamino)ethoxy-4-methoxyphenyl]-3-iodobenzamide;
N-[4-(2-Diisopropylamino)ethoxy-phenyl]-3-iodobenzamide;
N-[4-(2-Diisopropylamino)ethoxy-phenyl]-3-bromobenzamide;
N-[4-(2-Diisopropylamino)ethoxy-phenyl]-4-(cyclohexyl)benzamide;
N-[3-(2-Diisopropylamino)ethoxy-4-methoxy-phenyl]-4-(cyclohexyl)benzamide;
N-[3-(2-Diethylamino)ethoxy-4-methoxyphenyl]-4'-ethyl-[1,1'-biphenyl]-4-carboxamide;
N-[3-(2-Diisopropylamino)ethoxy-phenyl]-4'-ethyl-[1,1'-biphenyl]-4-carboxamide;
N-[3-(2-Dimethylamino)ethoxy-4-methoxyphenyl]-3'-methoxy-[1,1'-biphenyl]-4-carboxamide);
N-[3-(2-Diisopropylamino)ethoxy-phenyl]-2'-methyl-4'-(5-methyl-1,2,4-oxadiazol-3-yl)-(1,1'-biphenyl)-4-carboxamide;
N-[3-(2-Diisopropylamino)ethoxy-4-methoxyphenyl]-2'-methyl-4'-(5-methyl-1,2,4-oxadiazol-3-yl)-(1,1'-biphenyl)-4-carboxamide;
5-[4-(2-methyl-4-(5-methyl-1,2,4-oxadiazol-3-yl)phenyl)benzoylamino]spiro[(2,3-dihydrobenzofuran)-3,4'-(1-methylpiperidine)]oxalate;
N-[3-(2-Diisopropylamino)ethoxy-4-methoxyphenyl]-(1,1'-biphenyl)-4-carboxamide;
N-[3-(2-Diisopropylamino)ethoxy-4-methoxyphenyl]-2'-methyl-(1,1'-biphenyl)-4-carboxamide;
N-[3-(2-Diisopropylamino)ethoxy-phenyl]-2'-methyl-4'-(5-methyl-1,2,4-oxadiazol-3-yl)-[1,1'-biphenyl]-4-carboxamide;
N-[3-[2-(N-Cyclohexyl-N-isopropylamino)ethoxy]-4-methoxyphenyl]-[1,1'-biphenyl]-carboxamide;
N-[3-[2-(cis-2,6-Dimethylpiperidin-1-yl)ethoxy]-4-methoxyphenyl]-[1,1'-biphenyl]-4-carboxamide;
N-[3-[2-(N-Ethyl-N-isopropylamino)ethoxy]-4-methoxyphenyl]-[1,1'-biphenyl]-4-carboxamide;
N-[3-[2-(2,5-Dimethypyrrolidin-1-yl)ethoxy]-4-methoxyphenyl]-[1,1'-biphenyl]-4-carboxamide;
N-[4-Methoxy-3-[2-(2,2,6,6-tetramethylpiperidin-1-yl)ethoxy]phenyl]-1,1'-biphenyl-4-carboxamide;
N-[3-[2-(N-t-Butyl-N-isopropyl)aminoethoxy]-4-methoxyphenyl]-[1,1'-biphenyl]-4-carboxamide;
N-[3-(3-Diisopropylamino)propyloxy-4-methoxyphenyl]-[1,1'-biphenyl]-4-carboxamide;
N-[3-(3-Diisopropylamino)propyl-4-methoxyphenyl]-[1,1'-biphenyl]-4-carboxamide;
N-[3-(2-Diisopropylamino)ethoxy-4-iodophenyl]-[1,1'-biphenyl]-4-carboxamide;
N-[3-(2-Diisopropylamino)ethoxy-4-methoxyphenyl]-[1,1'-biphenyl]-4-methanamine Dihydrochloride;
N-[3-(2-Diisopropylamino)ethoxy-4-methoxy-phenyl]-4'-cyano-1,1'-biphenyl-4-carboxamide;
N-[3-(2-Diisopropylamino)ethoxy-4-methoxyphenyl]-4'-cyano-2'-methyl-1,1'-biphenyl-4-carboxamide;
N-[3-[2-(N-Isopropyl-N-methylamino)ethoxy]-4-methoxyphenyl]-[1,1'-biphenyl]-4-carboxamide;
N-[3-(2-Diisopropylamino)ethoxy-4-methoxyphenyl]-4-(iodo)benzamide;
N-[3-(2-Diisopropylamino)ethoxy-4-methoxy-phenyl]-4-(cyclohexyl)benzamide;
N-[3-(2-Diisopropylamino)ethoxy-4-methoxyphenyl]-4'-ethyl-[1,1'-biphenyl]-4-carboxamide;
N-[3-(2-Diisopropylamino)ethoxy-4-methoxyphenyl]-3'-methoxy-[1,1'-biphenyl]-4-carboxamide;
N-[3-(2-Diisopropylamino)ethoxy-4-methoxyphenyl]-4'-acetyl-[1,1'-biphenyl]-4-carboxamide;
N-[3-(2-Diethylamino)ethoxy-4-methoxyphenyl]-3'-methoxy-[1,1'-biphenyl]-4-carboxamide;
N-[3-(2-Diisopropylamino)ethoxy-4-methoxyphenyl]-3'-hydroxy-[1,1'-biphenyl]-4-carboxamide;
N-[3-(2-Dimethylaminoethoxy)-4-methoxyphenyl]-4'-(5-dimethylamino-1,2,4-oxadiazol-3-yl)-2'-methylbiphenyl-4-carboxamide;
N-[3-(1-Methylazetidin-2-ylmethoxy)-4-methoxyphenyl]-4'-(5-methyl-1,2,4-oxadiazol-3-yl)-2'-methylbiphenyl-4-carboxamide;
[7-(2-Dimethylaminoethoxy)-6-methoxy-3,4-dihydro-2H-quinolin-1-yl]-[2'-methyl-[1,2,4]-oxadiazol-3-yl)biphenyl-4-yl]-methanone oxalate;
2,3,6,7-Tetrahydro-1'-methyl-5-[2'-methyl-4'-(5-methyl-1,2,4-oxadiazol-3-yl)biphenyl-4-carbonyl]-furo[2,3-f]indole-3-spiro-3'-piperidine oxalate;
N-[2-(2-Dimethylamino)ethoxy-phenyl]-[1,1'-biphenyl]-4-carboxamide;
N-[3-(2-Diisopropylamino)ethoxy-4-methoxyphenyl]benzamide;
N-[3-(2-Diisopropylamino)ethoxy-4-methoxyphenyl]-[1,1'-biphenyl]-2-carboxamide;
N-[3-(2-Diethylamino)ethoxy-4-methoxyphenyl]-4-(methoxy)benzamide;
N-[3-(2-Diethylamino)ethoxy-4-methoxyphenyl]-4-(nitro)benzamide;
N-[3-(2-Diethylamino)ethoxy-4-methoxyphenyl]-4-(nitro)benzamide;
N-[3-(2-Dimethylamino)ethoxy-4-methoxyphenyl]-4-(nitro)benzamide;
N-[3-(Dimethylamino)ethoxy-4-methoxyphenyl]-[1,1'-biphenyl]-4-carboxamide;
N-[3-(2-Dimethylamino)ethoxy-4-methoxyphenyl]-4'-chloro-[1,1'-biphenyl]-4-carboxamide;
N-[3-(2-Diethylamino)ethoxy-4-methoxyphenyl]-4'-hydroxy-[1,1'-biphenyl]-4-carboxamide;
N-[3-(2-Diethylamino)ethoxy-4-methoxyphenyl]-4'-acetyl-[1,1'-biphenyl]-4-carboxamide;
N-[3-(2-Dimethylamino)ethoxy-4-methoxyphenyl]-4'-acetyl-[1,1'-biphenyl]-4-carboxamide;
N-[3-(2-Dimethylamino)ethoxy-4-methoxyphenyl]-3'-chloro-[1,1'-biphenyl]-4-carboxamide;
N-[3-(2-Diethylamino)ethoxy-4-methoxyphenyl]-3'-nitro-[1,1'-biphenyl]-4-carboxamide;
N-[3-(2-Dimethylamino)ethoxy-4-methoxyphenyl]-3'-nitro-[1,1'-biphenyl]-4-carboxamide;

N-[3-(2-Diethylamino)ethoxy-4-methoxyphenyl]-4-iodobenzamide;
N-[4-(2-Diethylamino)ethoxy-phenyl]-4-iodobenzamide;
N-[2-(2-Diisopropylamino)ethoxy-phenyl]-4-iodobenzamide;
N-[4-(2-Diethylamino)ethoxy-phenyl]-3-iodobenzamide;
N-[2-(2-Diisopropylamino)ethoxy-phenyl]-3-iodobenzamide;
N-[2-(2-Diethylamino)ethoxy-phenyl]-3-iodobenzamide;
N-[3-(2-Diethylamino)ethoxy-phenyl]-4-bromobenzamide;
N-[2-(2-Diisopropylamino)ethoxy-phenyl]-4-bromobenzamide;
N-[2-(2-Diethylamino)ethoxy-phenyl]-4-bromobenzamide;
N-[4-(2-Diethylamino)ethoxy-phenyl]-3-bromobenzamide;
N-[2-(2-Diisopropylamino)ethoxy-phenyl]-3-bromobenzamide;
N-[2-(2-Diethylamino)ethoxy-phenyl]-3-bromobenzamide;
N-[3-(2-Diethylamino)ethoxy-4-methoxyphenyl]-4-(dimethylamino)benzamide;
N-[4-(2-Diisopropylamino)ethoxy-phenyl]-4-(dimethylamino)benzamide;
N-[4-(2-Diethylamino)ethoxy-phenyl]-4-(dimethylamino)benzamide;
N-[2-(2-Diisopropylamino)ethoxy-phenyl]-4-(dimethylamino)benzamide;
N-[2-(2-Diethylamino)ethoxy-phenyl]-4-(dimethylamino)benzamide;
N-[4-(2-Diethylamino)ethoxy-phenyl]-4-(isopropyl)benzamide;
N-[2-(2-Diisopropylamino)ethoxy-phenyl]-4-(isopropyl)benzamide;
N-[2-(2-Diethylamino)ethoxy-phenyl]-4-(isopropyl)benzamide;
N-[3-(2-Diethylamino)ethoxy-phenyl]-4-(cyclohexyl)benzamide;
N-[2-(2-Diisopropylamino)ethoxy-phenyl]-4-(cyclohexyl)benzamide;
N-[2-(2-Diethylamino)ethoxy-phenyl]-4-(cyclohexyl)benzamide;
N-[2-(2-Diisopropylamino)ethoxy-phenyl]-4'-ethyl-[1,1'-biphenyl]-4-carboxamide; and
N-[2-(2-Diethylamino)ethoxy-phenyl]-4'-ethyl-[1,1'-biphenyl]-4-carboxamide.

3. The method as claimed in claim 1, wherein the disease is selected from COPD, asthma and atopic disorders, rheumatoid arthritis, sarcoidosis and other fibrotic diseases, atherosclerosis, psoriasis, autoimmune diseases such as multiple sclerosis, inflammatory bowel disease, and HIV infection.

* * * * *